United States Patent [19]

Waska et al.

[11] Patent Number: 5,312,535
[45] Date of Patent: May 17, 1994

[54] CAPILLARY ELECTROPHORESIS DETECTION

[75] Inventors: Frank L. Waska, Brea; Gerald L. Klein, Orange; Wayne S. Johnson, La Habra, all of Calif.

[73] Assignee: Beckman Instruments, Inc., Fullerton, Calif.

[21] Appl. No.: 917,640

[22] Filed: Jul. 17, 1992

[51] Int. Cl.$^5$ .............................................. C25B 9/00
[52] U.S. Cl. ........................... 204/299 R; 356/344; 356/441
[58] Field of Search ........................ 356/344, 441; 204/299 R

[56] References Cited

U.S. PATENT DOCUMENTS

| | | | |
|---|---|---|---|
| 3,864,044 | 2/1975 | Lyshkow | 356/201 |
| 4,534,651 | 8/1985 | Minikane | 356/440 |
| 4,675,300 | 6/1987 | Zare et al. | 436/172 |
| 4,804,267 | 4/1989 | Greenfield | 356/335 |
| 4,816,123 | 3/1989 | Ogan et al. | 204/183.3 |
| 4,898,658 | 2/1990 | Karger et al. | 204/299 R |
| 4,927,265 | 5/1990 | BrownLee | 356/73 |
| 4,940,883 | 7/1990 | Karger et al. | 219/210 |
| 4,989,942 | 2/1991 | Koenigsberg et al. | 350/96.18 |
| 5,007,740 | 4/1991 | Jeannotte et al. | 356/436 |
| 5,019,236 | 5/1991 | Young | 204/299 R |
| 5,037,523 | 8/1991 | Weinberger et al. | 204/299 R |
| 5,061,361 | 10/1991 | Gordon | 204/299 R |
| 5,066,382 | 11/1991 | Weinberger et al. | 204/299 R |

OTHER PUBLICATIONS

Journal of Chromotography, 480 (1989) 185-196 Elsevier Science Publisher B. V., Amsterdam, by Michael J. Sepaniak, David F. Swaile & A. Craig Powell, "Instrumental Developments in Micellar Electrokinetic Capillary Chromatography".

Sepaniak et al., "Instrumental Developments in Micellar Electrokinetic Capillary Chromatography", *Journal of Chromatography* 480:185-196 (1989).

Foret et al., "On-Line Fiber Optic UV Detection Cell and Conductivity Cell for Capillary Zone Electrophoresis", *Electrophoresis*, 7:430-432 (1986).

Primary Examiner—John Niebling
Assistant Examiner—C. Delacroix-Muirheid
Attorney, Agent, or Firm—William H. May; Gary T. Hampson; Charles Berman

[57] ABSTRACT

Detecting light in a capillary electrophoresis optical system includes input and output windows in the outside surface of a capillary tube. The width of the windows is not substantially greater than the bore of the tube. A fiber optic input is spaced from the capillary tube so that the light is directed to the tube and is matched to the window width. The light output from the tube is matched to be received by a fiber optic output spaced from the capillary tube. The optical light envelop from the fiber input through the tube and to the fiber output is governed by the LaGrange Invariant. The matching is effected in accordance with the Numerical Aperture of the fiber optics.

58 Claims, 12 Drawing Sheets

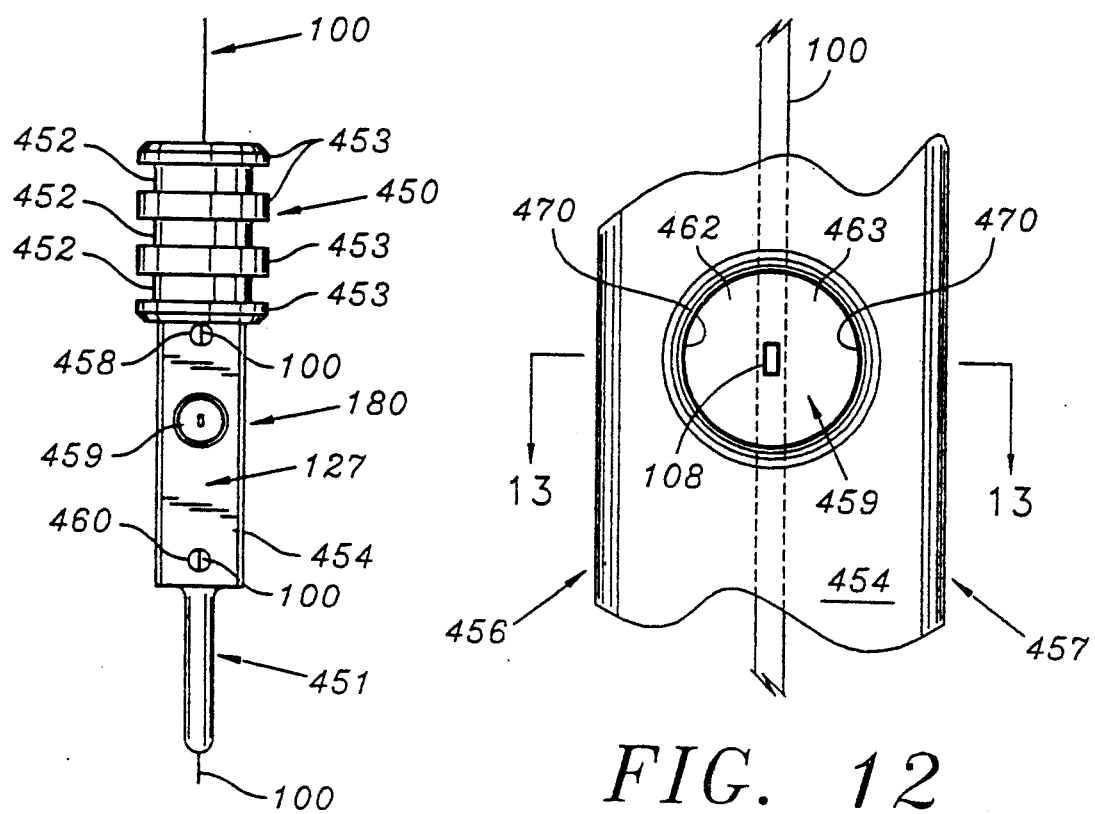
FIG. 11
FIG. 12
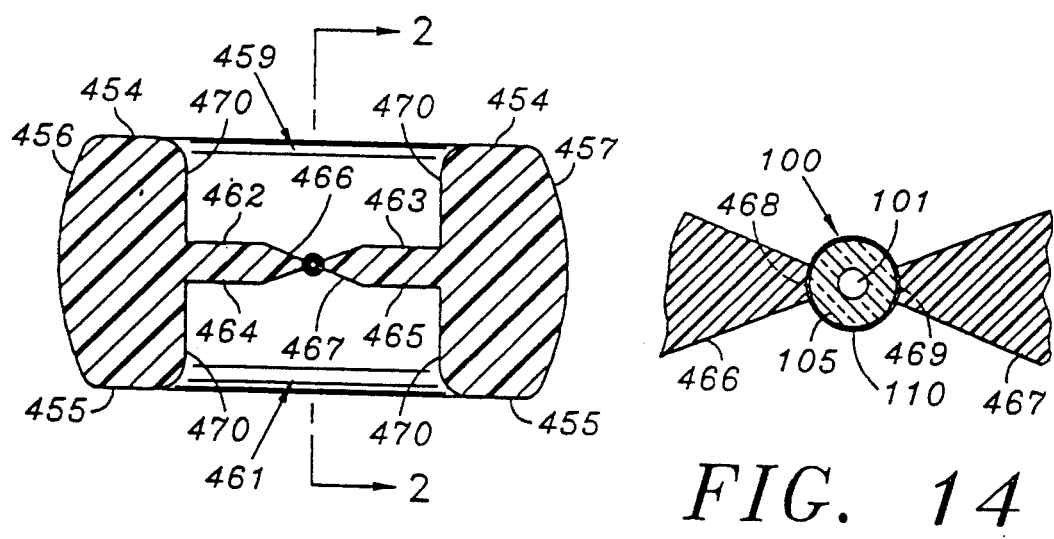
FIG. 13
FIG. 14

CAPILLARY ELECTROPHORESIS DETECTION

RELATED APPLICATION

This invention relates to Application Ser. No. 07/847,783, filed Mar. 5, 1992 and entitled "Fiber Optic Flow Cell for Detection of Electrophoresis Separation with a Capillary Column and Method of Making Same." The contents thereof are incorporated by reference herein.

BACKGROUND

Accurately detecting light in a capillary electrophoresis system is an increasingly vital procedure for the analysis of chemicals, cells and biological matter.

This invention relates to a capillary electrophoresis system, particularly where light through a capillary tube is optically detected. More specifically, the invention relates to the precise detection of light output from such a capillary electrophoresis system. Additionally, the invention is concerned with optimizing light energy input to and output from a capillary electrophoresis tube so that, overall, there is obtained a highly sensitive capillary electrophoresis system.

Electrophoresis is an analytical technique whereby small volumes of mixed sample solution are separated by differences in electric charges and molecular sizes of individual sample components. Capillary electrophoresis requires the transportation of small, often minute, quantities of sample solution through a capillary tube under pressure or electrical differential. As the sample travels though the capillary tube, a separation of components of the sample is effected due to the differential.

A light source and a light detector are placed outside the capillary tube which is mounted in a support. As the sample, so separated, migrates through the capillary tube, light is passed along an optical path across the sample. By detecting the light output, information about the nature, for instance, the chemical make-up, of the sample can be obtained.

The capillary electrophoresis tube is a microbore tube and is used as the support and means for transporting liquid containing the sample. Typically, the dimension of the capillary bore diameter ranges from 5 to 500 microns. The shape usually employed for the capillary tube is cylindrical and the wall thicknesses of the tube ranges from 25 to 200 microns.

The nature of the walls of the capillary tube provide different refraction indices and generally cause inaccuracies in the light which is received by the detector. To provide accurate results, however, it is important to avoid optical problems such as distortions to the light caused by perturbations and wall effects of the tube.

The small sizes encountered in the capillary dimensions pose severe problems for accurate optical detection. These include problems arising from the short pathlength through the sample.

Detection of the separated components requires a measurable property of the component. Absorbance, for instance, is measured as the relative decrease in the intensity of the light at a selected wavelength passing through the sample due to the relative concentration of the sample being measured, its specific absorbtivity, and pathlength.

Absorbance is expressed by the Beer-Lambert-Bourgier Law:

$$A = kcl$$

where
A = Absorbance
k = molar extinction coefficient
c = concentration of the absorbing sample
l = pathlength through sample When the pathlength becomes smaller, as is encountered with the minute capillary dimensions typically used, the magnitude of the Absorbance decreases.

With the circular cross section of the bore of the capillary tube, the pathlength also varies sinusoidally as light passes transversely through the capillary bore. The pathlength at the poles is zero, and is a maximum length at the equator.

Another problem occurs when light from the light source passes through the solid wall material of the capillary tube without passing through the sample solution in the bore of the tube. This light, termed stray light, contributes to the light energy arriving at the detector without having been attenuated by the absorbing sample.

Additional problems arise in the optical system for detection of solution volumes at the tiny dimensions used for capillaries. To assure reproducible reliable determinations of detected light, the capillary tube must be positioned in the optical system rigidly and accurately. It is difficult and costly to achieve the mechanical tolerances required to meet these conditions where the bore of the tube is movable relative to the window for light that enters the bore.

There is a need to provide a system which can provide accurate data and information within modern detail standards and yet have relaxed precision mechanical tolerances and requirements.

The prior art has used optical systems and optical devices such as lenses and slits in the optical path to improve the optical system. These devices themselves create optical distortions and changes, such as dispersion, to the light. Further inaccuracies are thus created in the detected light.

There is a need to provide a system with a minimum number of optical elements and devices between the signal input and the detected signal.

Light for the optical system is obtained and received through fiber optical input and output. The fiber optic has a core and cladding which have different refractive indices, and the light is propagated in the fiber core. An Angle of Acceptance of the fiber is the half-angle of an Acceptance cone of the fiber. This is the angle about the central axis of the fiber. It is also the angle at the interface of the core and cladding, namely, the Angle of Acceptance is defined by the difference in the refractive index of the core and cladding. Light entering a fiber at angles greater than the acceptance angle leak away and are not propagated to the output end of the fiber optic. Similarly, light normally does not exit a fiber at an angle greater than the Angle of Acceptance.

A Numerical Aperture of the fiber is related to the Angle of Acceptance through the fiber, and is a measure of light-gathering power of the fiber optic. The Numerical Aperture is the sine of the Angle of Acceptance for the fiber.

Prior art systems have not been able to optimize the optical system and the relationship of light generation and propagation in a fiber optic and the detection characteristics in capillary electrophoresis systems.

There is a need for an improved capillary electrophoresis detection system having less distortion of light, and which is easily configured with the fiber optics of the optical system. Also, there is a need for a system which optimizes the use of the light energy from a fiber optic as measured by the Numerical Aperture into the capillary electrophoresis tube. Further, there is in turn, the need for the output from the capillary electrophoresis tube to be related to a receiving fiber optic so as to maximize the receipt of the light from the tube as measured by the Numerical Aperture of the receiving fiber optic.

SUMMARY

The present invention provides an optical system for capillary electrophoresis which markedly improves the characteristics of capillary electrophoresis detection and of the optical system. The invention significantly minimizes multiple problems encountered with prior art systems.

The invented system provides a capillary electrophoresis system comprising a capillary tube having a bore that transports sample fluid past a detection path, namely an optical path. An inner surface of the bore defines a selected diameter. A wall thickness is defined between the inner surface and an outer surface. The optical path is defined so that light between an optical input window and an optical output window to the tube does not pass through the wall without additionally passing through the bore.

The input window is provided preferably on an outer surface portion of the tube and the output window is provided preferably on an opposite outer surface portion of the tube. The tube is opaque to light passage through the bore at one or more selected wavelengths except at the windows, which are discretely shaped and located relative to the capillary tube bore.

At least one of the input window or output window defines an aperture width and the aperture width is substantially no greater than the bore diameter. "Opposite" is considered as positions diametrically opposed to each other.

With this configuration, substantially only the critical and optimized light passes into the tube through the bore and out of the tube. The sample passing in the bore can be detected with substantially improved accuracy and detail.

Preferably, both apertures have a width substantially no greater than the bore diameter and preferably are configured to be of a substantially equal width as the bore diameter. The width of both apertures is preferably equal to the bore diameter.

The aperture width is preferably defined by respective straight lines directed adjacently from respective interfaces between an input window and the outer surface of the bore to the respective opposite interfaces between an output window and the outer surface of the bore. Each respective line passes radially through a central longitudinal axis of the bore, and each respective straight line adjacent respectively opposite interfaces defining the width of the input window and output window.

A LaGrange Invariant is an optical Invariant which is related to the aperture of light in the optical path, is a constant for the optical path, and is defined by the maximum aperture in the optical path.

In one form of the invention, the width of the windows also defines an optical aperture width which is established in terms of a LaGrange Invariant. In another form of the invention, the diameter of the bore and at least one, and preferably both, windows define the optical aperture width in terms of the LaGrange Invariant.

The Invariant for the input and output apertures are retained at a relatively high value, preferably as high as possible. The higher the Invariant, the greater the amount of light energy passing through the bore. The Invariant is consistent through at least the optical path between the input window and output window. The value of the LaGrange Invariant is determined by substantially the diameter of the capillary bore. Since the diameter is preferably equal to the window width, the LaGrange Invariant is also defined by the window width.

In the present invention, the Invariant is also defined by the angle between the line from a window interface to the bore center to either side of a transverse axis along the optical path through the bore center. It is the substantially maximum angle for receiving light in the bore relative to the least light through the tube wall. By having the window width, namely, the aperture width so defined, substantially only the critical light passes through the capillary bore and then reaches the output window. Light which would otherwise render the detection inaccurate is masked out of the capillary electrophoresis system between input and output.

The LaGrange Invariant defines the location and width of the windows, and also the ratio of the fiber end diameter and the window width. As such, the LaGrange Invariant defines the extremities of the optical system and the optical envelop or optical caustic.

In a preferred form of the invention, there is provided a fiber optic input for directing an input signal, namely light, to the input window and a fiber optic input for receiving light from the output window. The light from the fiber input falls within both a diverging cone and a converging cone of light, the conical half angle being the Angle of Acceptance of the fiber. Similarly, light into the output fiber is received in a converging cone and a diverging cone, also defined by its respective Angle of Acceptance. Thus, the angles of the respective converging and diverging cones are established by the Angles of Acceptance of the fibers. The converging input cone from the fiber input and the diverging cone for the fiber output are matched with the optical path of the capillary tube.

The fiber input includes an end which is spaced a selected distance from the input window whereby the width of the converging cone containing the light rays from the fiber input end face defines a converging angle cone which substantially matches or mates with the width of the input window.

The spacing of the end of the input fiber is also such that the cross-sectional area of the converging cone at the end of the input fiber is established by the LaGrange Invariant of the capillary electrophoresis tube.

The output light from the capillary falls within an angle substantially equal to the Angle of Acceptance of the fiber optic output. The spacing of the receiving end face of the fiber output from the output window is such that the diverging cone of light exiting from the tube defines a width so that it constitutes at least a substantially equal cross-section of the receiving end face of the core of the fiber output. This relationship of a diverging output cone is set up in matching relation to the LaGrange Invariant of the capillary tube.

The apex of the converging cone from the fiber input is directed inwardly into the tube and is located preferably at or towards the center of the bore. The apex of the diverging cone to the fiber output is also located preferably at or towards the center of the bore.

The tube outer surface normally includes a confromal coating of a polymer which is opaque to light energy at the ultraviolet wavelength. The input and output windows are formed by selectively removing at least this coating by a laser. Ideally, the windows should be located as close to the bore as possible to minimize interference with the light. To this end, a portion of the wall can in some cases also be removed to locate the inside of the window closer to the bore.

Preferably, the capillary tube is rigidly mounted in a holder with the tube secured and held by flashing elements from the molding process for fabricating the holder. Thereafter, laser energy is precisely applied to cut the windows in sequence. The input window and output window are selectively formed in turn. This effectively creates a masking to the ultraviolet wavelengths constituted by the coating while permitting the ultraviolet wavelengths to enter and leave the tubing through the windows.

By the present invention, there is provided an optical path which includes an input fiber, the capillary tube and an output fiber without the need for additional optical elements, such as lenses or slits, to focus or manipulate a light beam through the capillary tube. By having light pass from input fiber through air and directly into the glass constituting the capillary tube, distortion is minimized and detection accuracy is notably enhanced. By having the windows integrally formed in the tube wall, and the capillary tube rigidly fixed in the holder, the ease of optical and mechanical alignment of the electrophoresis system is markedly simplified.

This system provides for substantially more light to pass through the sample in the bore of the capillary tube and to the output window without passing through unnecessary parts of the tube and being available to provide for distortion of the required detected results of the sample.

By using the critical angle relationship as defined by the window and fiber characteristics, light containing information, namely light modulated by only the sample in the bore, passes to the output fiber. This permits for obtaining relevant sensitive detected information of the requisite sample. Also, the light output is obtained without distortion or aberrations caused by the optical elements.

The net result is a highly significantly improved optical system for capillary electrophoresis, with a substantial improvement in the efficiency of light transmission from the input through the tube and to the output.

The invention has application to wavelengths extending at least in the electromagnetic spectrum, and particularly from the infrared through visible to the ultraviolet wavelengths.

The invention is further described with reference to the accompanying drawings.

DRAWINGS

Figure 3A:
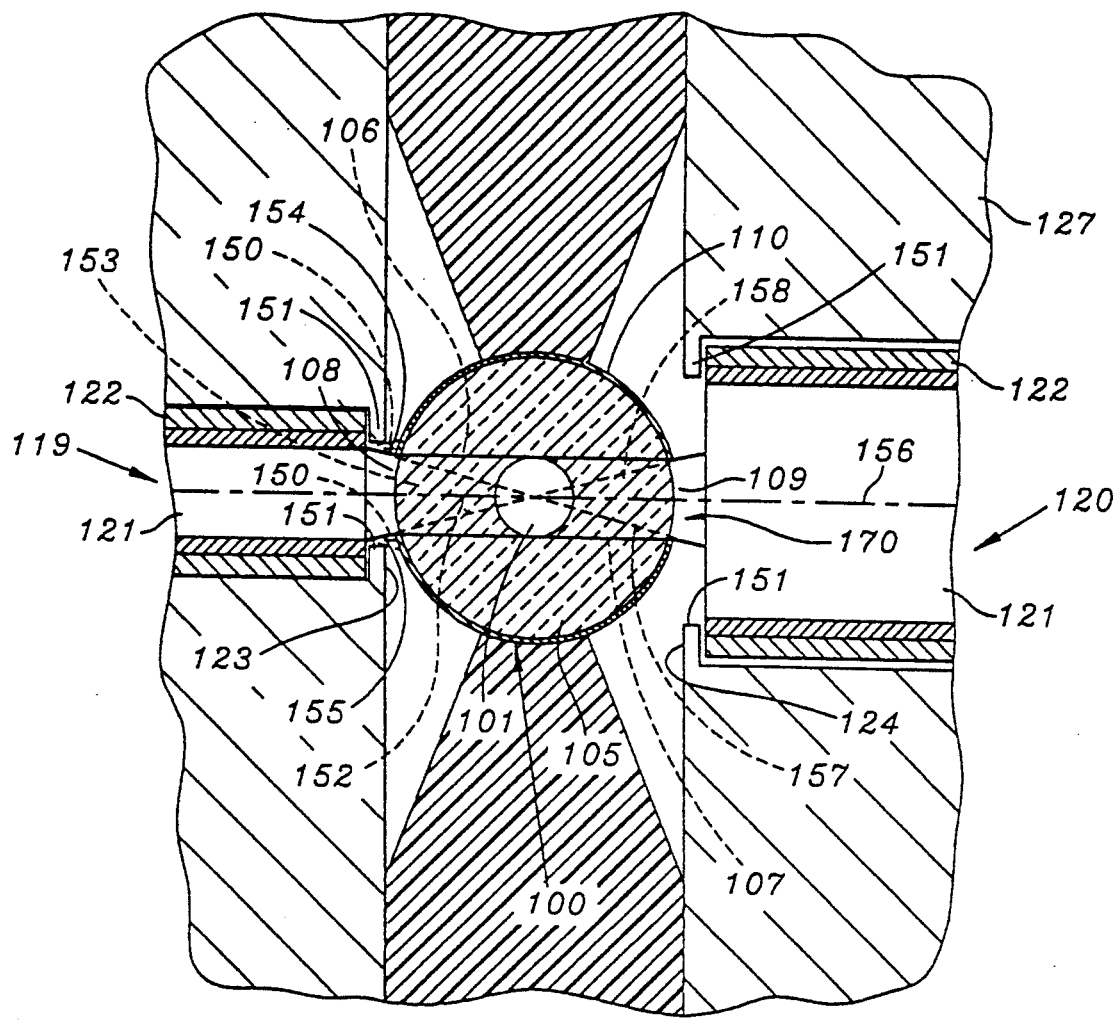
FIG. 3a is a cross-sectional end view through the optical system showing the end of the capillary tube with an input fiber and output fiber and illustrating an end view of the light envelop between the fibers and through the tube.
Figure 3B:
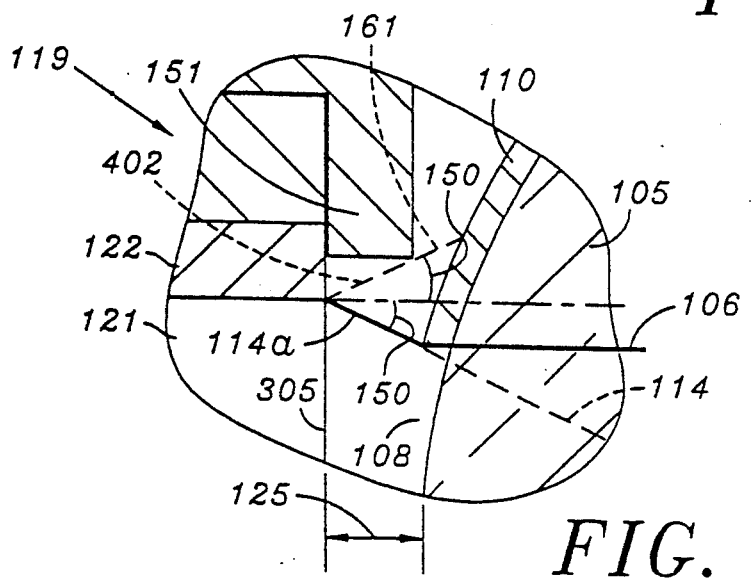
FIG. 3b is a detail illustrating the angular relationship at the input fiber relative to the capillary tube.
Figure 3C:
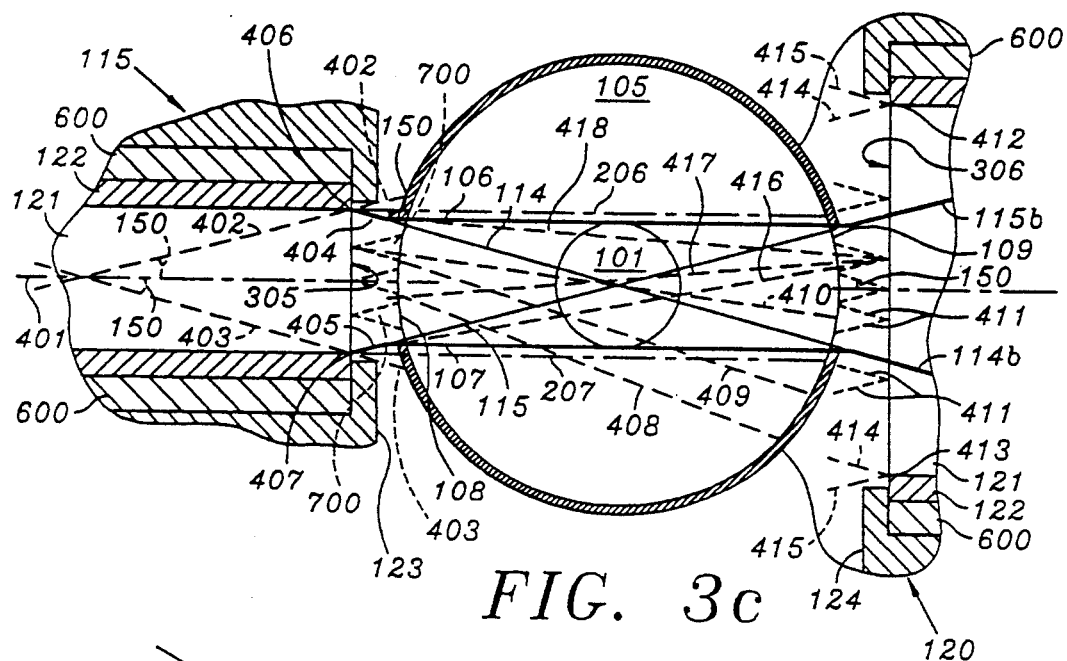

FIG. 3c is a cross-sectional end view showing representative optical light ray paths and the light envelop. The respective diverging and converging conical envelop from the input fiber is illustrated. Representative light rays from the input fiber end and light rays to the output fiber end are shown.

Figure 3D:
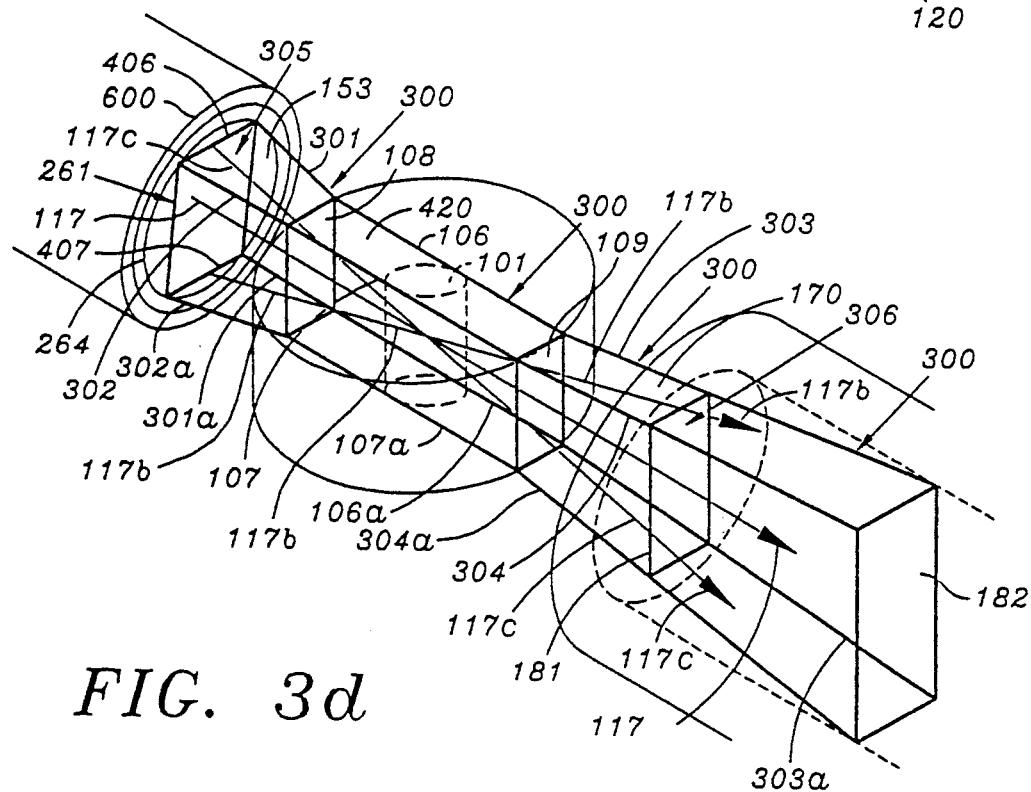

FIG. 3d is a perspective view of the optical system from the input fiber, through the capillary tube and into the output fiber. The light envelop or light caustic through which the input light from the end of the input fiber is illustrated. The envelop defines a width equal to the bore diameter. The envelop ensures that light leaving the capillary tube has passed through the bore containing the sample without bypassing the bore. Light leaving the tube then enters the receiving end of the output fiber.

Figure 4:
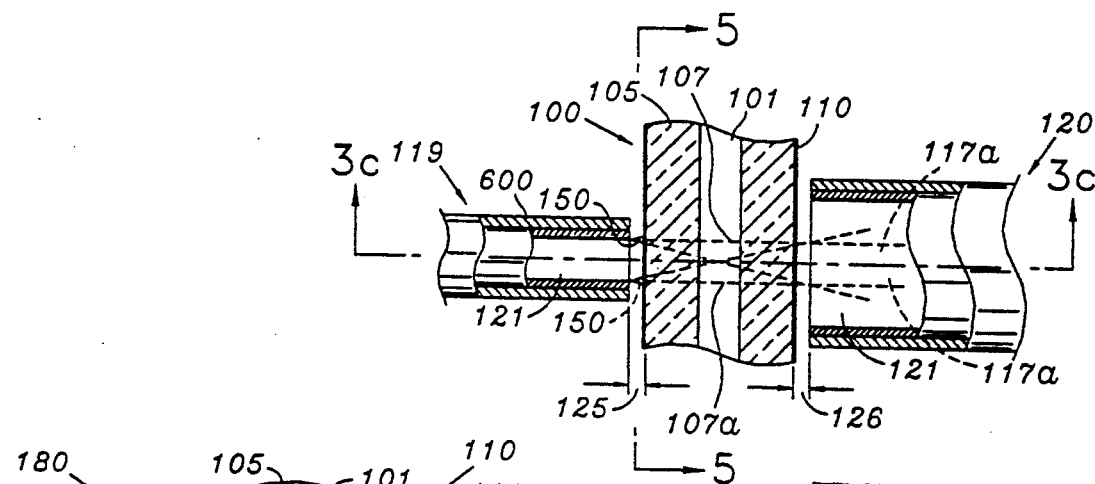

FIG. 4 is a cross-sectional optical side view of the capillary tube in relation to the input fiber and output fiber illustrating a side view of the light envelop between the fibers and through the tube.

Figure 5:
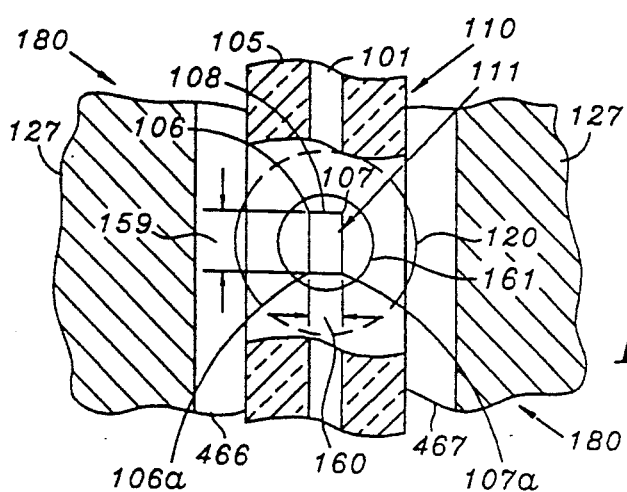

FIG. 5 is a partial side view similar to FIG. 4, the view of FIG. 4 being turned through 90° and showing the input window in the capillary tube.

Figure 6:
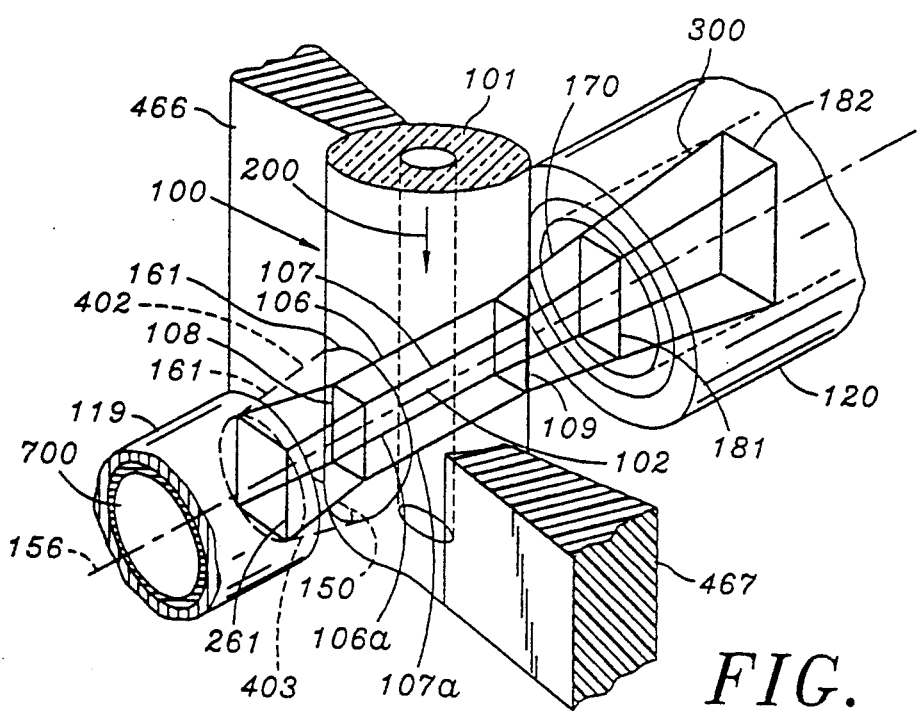

FIG. 6 is a partial perspective view similar to FIG. 3d but turned about the axis of the bore so that the input fiber viewed in the foreground. The light envelop is shown relatively with the input fiber, the capillary tube with a portion of the holder and the output fiber. There is a diverging conical envelop emerging from the input fiber shown in phantom lines. A converging envelop emanating at least partly from the interface of the core and cladding of the input fiber enters the input window. After passage of light in the envelop through the window, the envelop is contained within a regular cube within the capillary tube. Light emerges from the output window within a diverging envelop conforming to the rectangular cross-section. The light enters the output fiber optic with an increasing rectangular cross-section until it meets the cladding-core interface of the output fiber.

Figure 7:
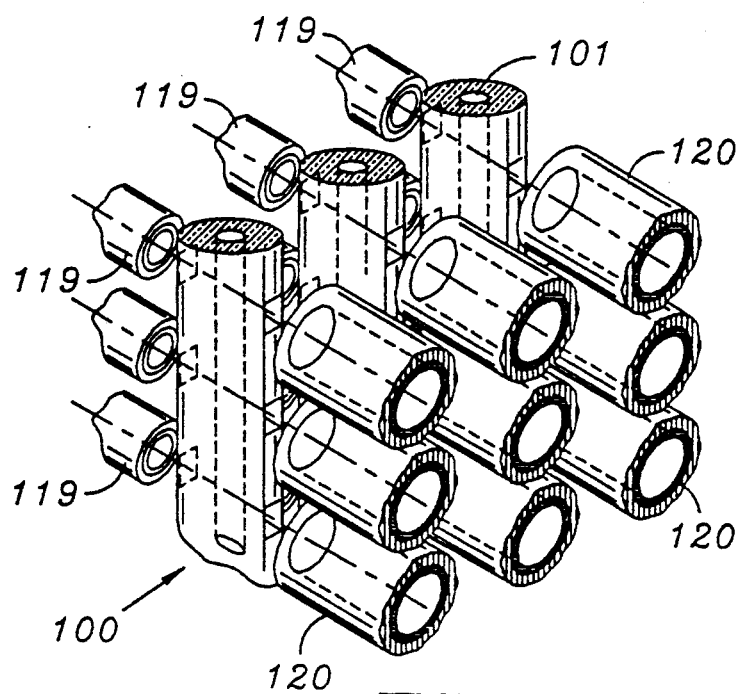

FIG. 7 is a partial perspective view illustrating multiple fiber optic inputs and outputs for multiple capillary tubes.

Figure 8:
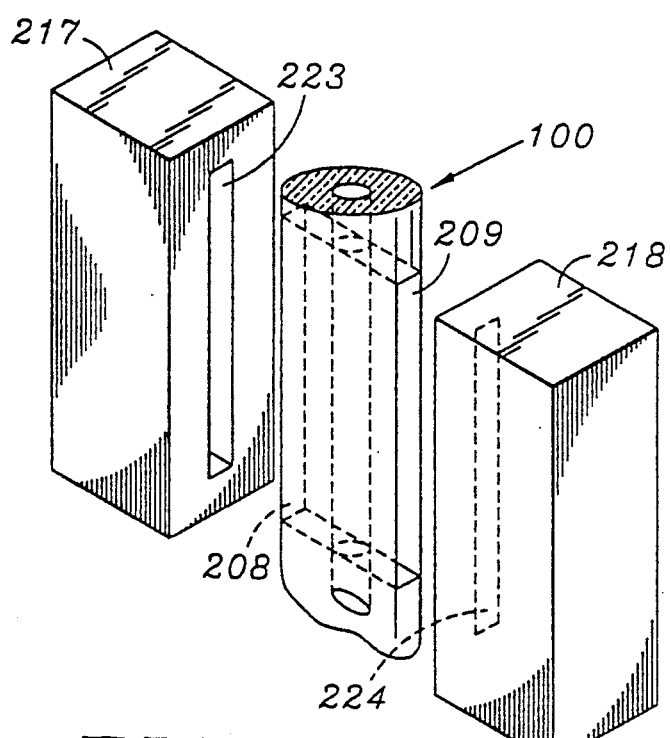

FIG. 8 is a partial perspective view illustrating a representative scanning light beam and a linear array detector.

Figure 9:
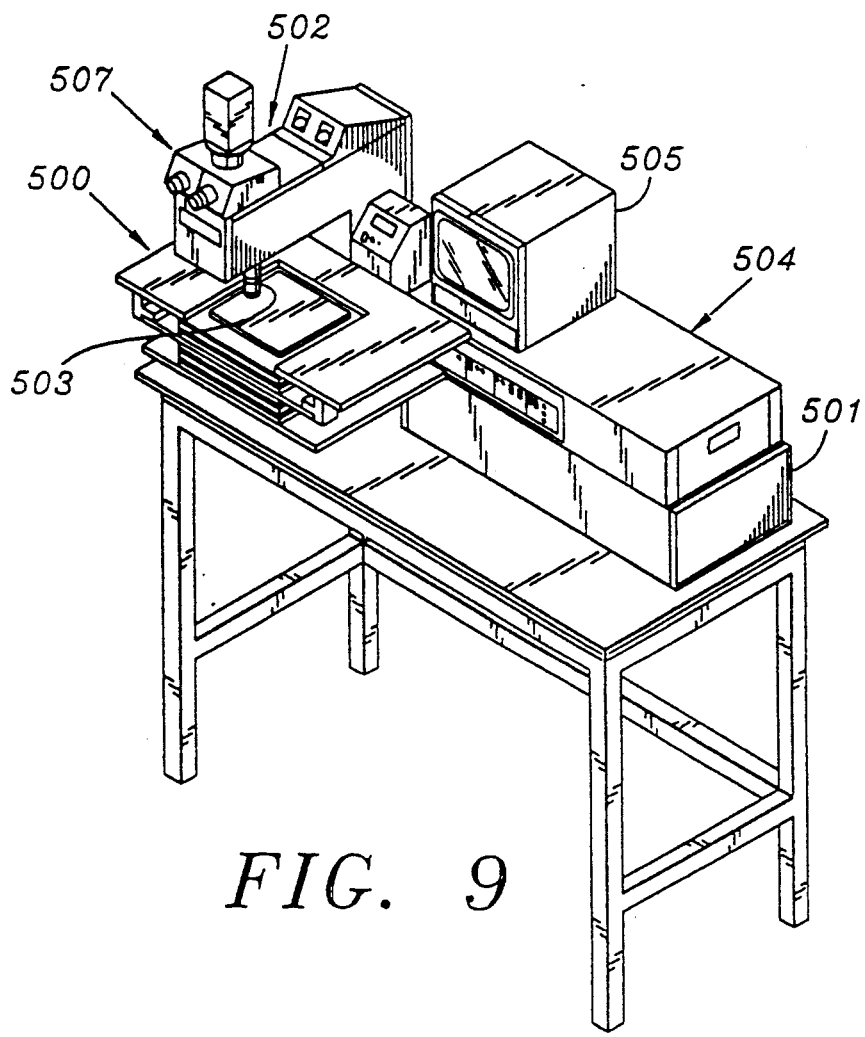

FIG. 9 is a perspective view of a laser for forming the windows in the capillary tube when the capillary tube is contained in a holder.

Figure 10:
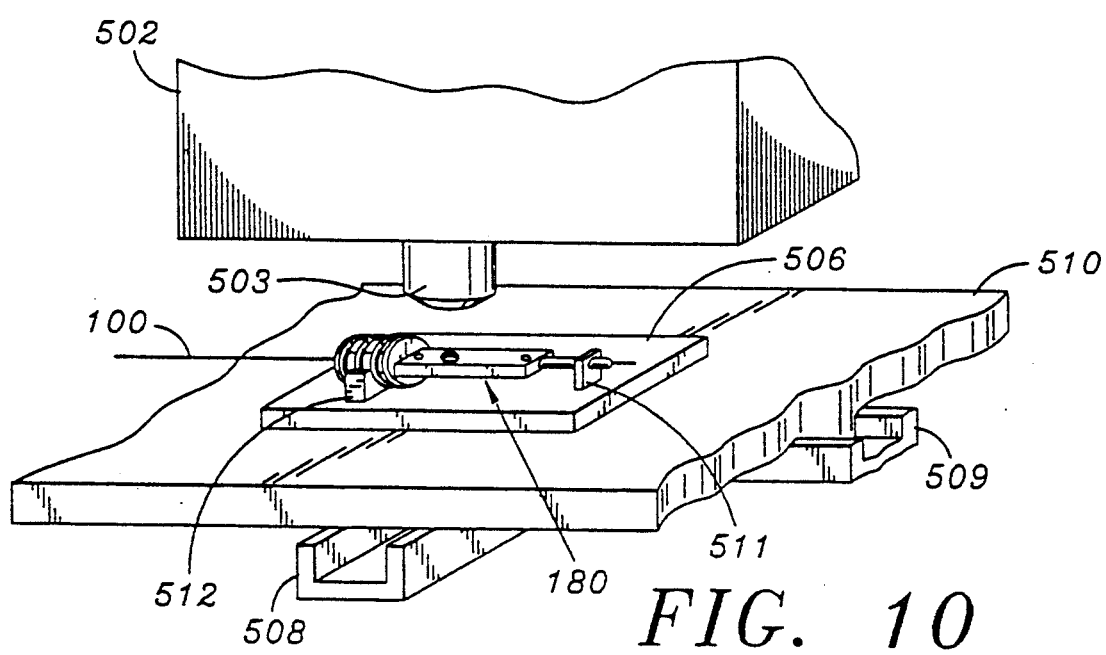

FIG. 10 is a perspective view of the holder secured to a platen below a laser beam output.

FIG. 11 is a front view of the holder illustrating the capillary tube passing through.

FIG. 12 is a detail of FIG. 11 illustrating the window area adjacent which the fiber optics would be located.

FIG. 13 is a cross-sectional end view along lines 13—13 of FIG. 12 illustrating the capillary tube in position in the window.

FIG. 14 is a detail of FIG. 13 illustrating the securing of the capillary tube in the window by the converging flashing sections directed from the sides of the holder towards the center.

Figure 15:
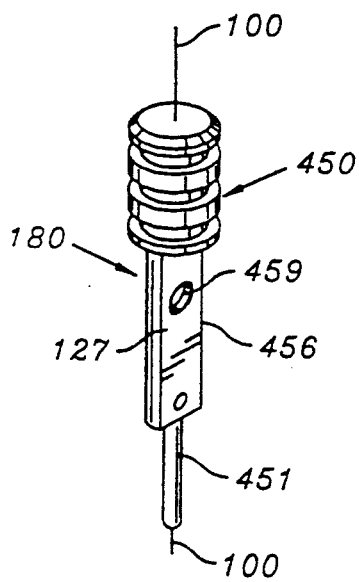

FIG. 15 is a perspective view of the holder viewed from the top.

Figure 16:
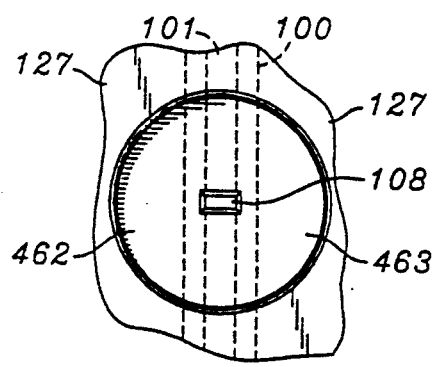

FIG. 16 is a partial front view of an alternative window configuration for the holder. The input window is relatively narrower in height compared to the width of the window.

Figure 17B:
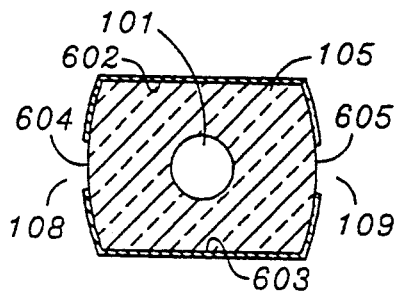
Figure 17A:
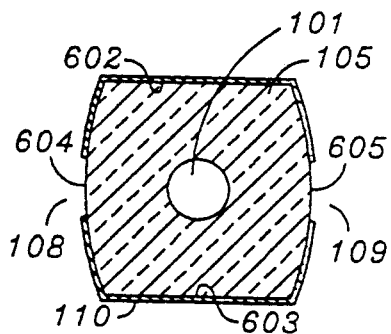
Figure 17C:
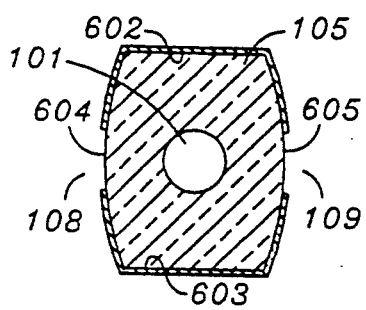
Figure 17D:
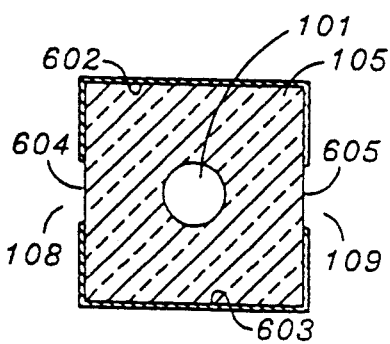
Figure 17E:
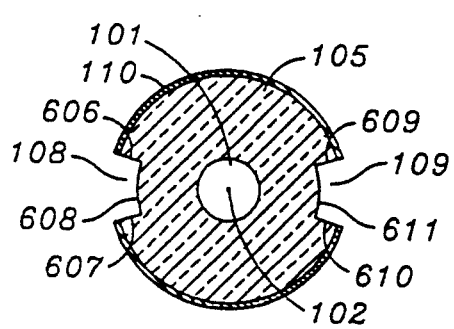

FIGS. 17a to 17e illustrate different cross-sections of the capillary tube with input and output windows. In FIG. 17e, the input window and output window is formed by removal of the polymer coating and a portion of the material forming the tube.

FIGS. 18a, 18b, 18c, 18d, 18e, 18f and 18g illustrate different capillary tubes with different thickness walls, different bore diameters and different coatings in relation to the Numerical Aperture of the input fiber optic and output fiber optic relative to the LaGrange Invariant characteristics.

Figure 19:
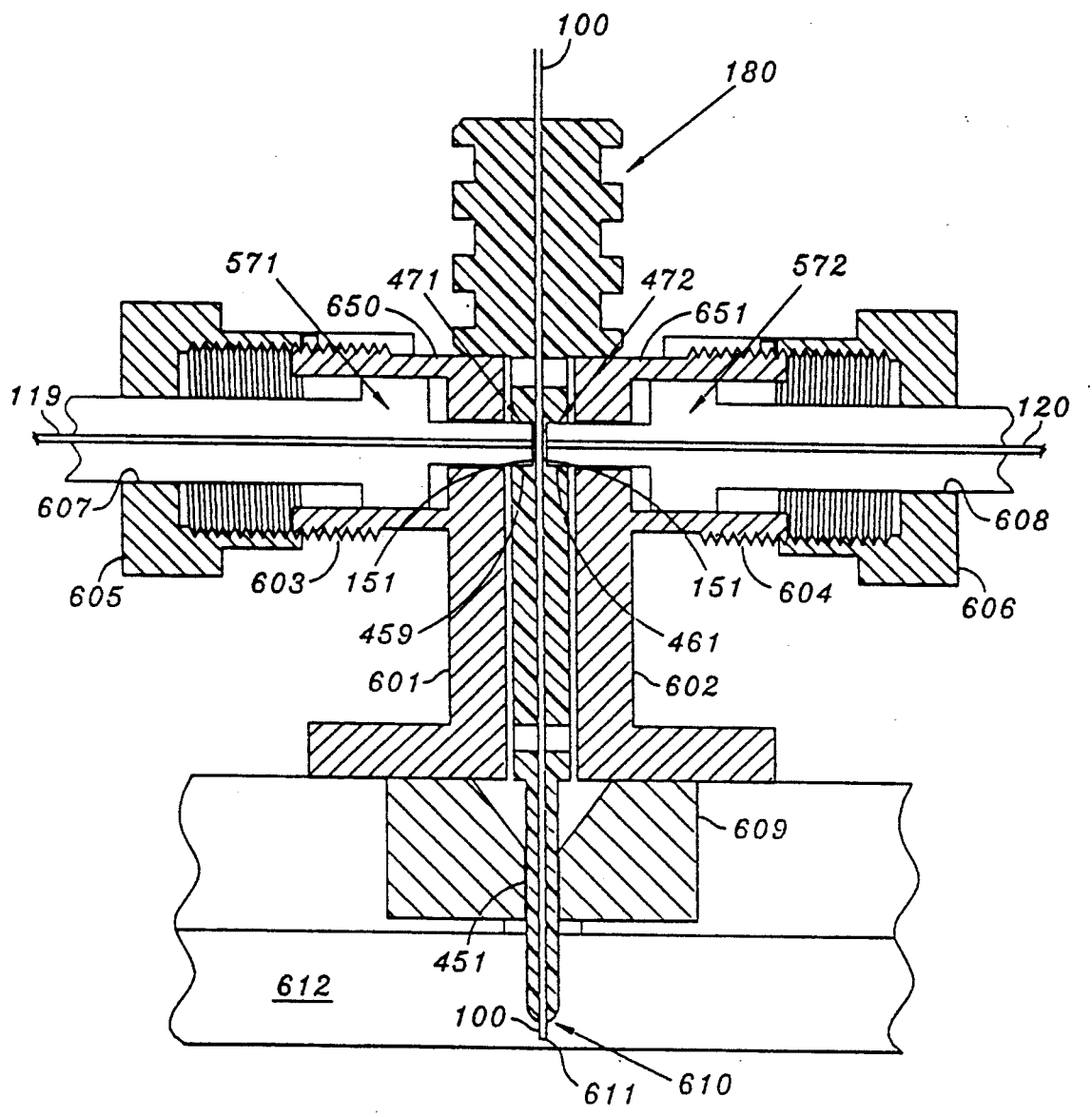

FIG. 19 is a sectional side view of the holder and capillary tube located in a system relative to the input fiber optic, output fiber optic and illustrating the elements for physically securing the holder and fiber optics relatively together.

Figure 20A:
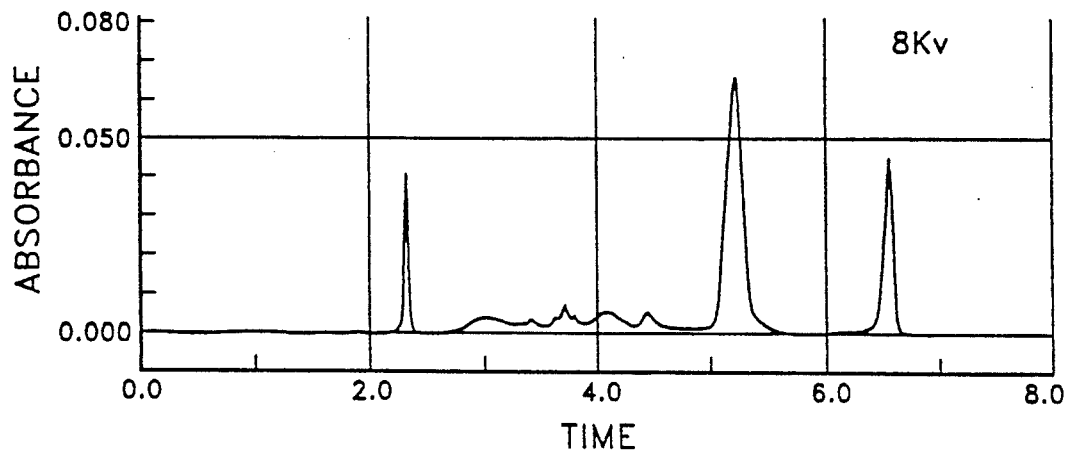
Figure 20B:
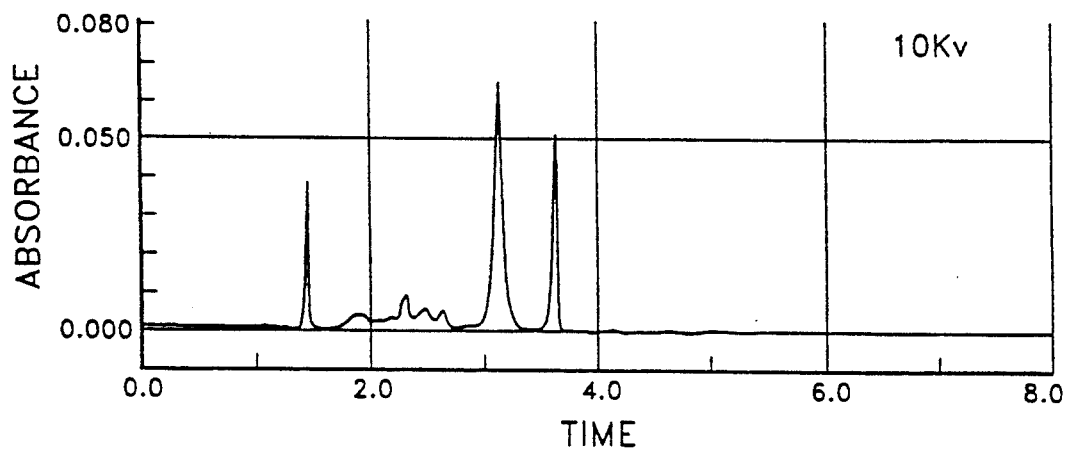

FIGS. 20a and 20b are data reflecting a plot of light absorbance against time at two different voltage differentials across the capillary electrophoresis tube.

DESCRIPTION

1. The Capillary Tube

A capillary electrophoresis system includes a capillary tube 100 of circular cross-section having a bore 101 of circular cross-section A fluid sample passes through bore 101 as indicated by arrow 200. The bore 101 includes a center 102 and an inner surface 103 which defines a bore width, namely the diameter for the bore 101. The capillary tube 100 includes an outer surface 104 and a wall 105. The thickness of the wall 105 is defined between the inner surface 103 and the outer surface 104. As defined, this thickness does not include a coating 110 at the outer surface 104.

The capillary tube 100 is formed of a silicone quartz glass having a refracted index of $n_1$. A thin confromal coating 110 of a polyimide, being a silicone, acrylate, or metallic, about 10 microns thick is provided about the outside surface 104 of the glass quartz forming the capillary tube 100. The coating 110 is opaque to ultraviolet energy in the range of about 200–300 nm which is used for detection in the electrophoresis optical system.

A typical capillary tube 100 is formed of fused silica and is flexible. It is capable of withstanding proof test pressures of up to about 75 kpsi. The coating 110 is operable at temperatures up to about 400° C. The preferred tube 100 is manufactured by Polymicro Technologies, Incorporated of Phoenix, Ariz.

2. The Windows

The sample fluid is transported in the bore 101 past a detection path, namely an optical path, which, when viewed from an end, is defined between parallel lines 106 and 107 which are spaced to either side of the bore 101, and are tangential or adjacent to the circumference of the bore 101. An optical input window 108 is provided on one side of the optical path. An optical output window 109 is provided on the opposite output side of the optical path.

The input window 108 and output window 109 are formed as a slit with a selected width and length. The windows 108 and 109 are formed by removing the opaque polyimide coating 110 at the area of the windows 108 and 109, respectively. This removal can be affected by mechanical removal, chemical etching, and laser trimming. An effective manner of manufacture is firstly to form a window 108. Thereafter, the tube 100 is turned through 180° around its longitudinal axis about center 102 and the window 109 is formed.

3. The Holder

The capillary tube 100 is mounted in a holder 180. The holder 180 is formed by an injection molding process and is constituted by a black plastic material. An advantage of having a black holder 180 is the increased ability of the holder 180 to absorb undesirable stray light or other energy.

The holder 180 is constituted by three major components: a cylindrical top portion 450, a middle essentially flat holder component portion 127, and a cylindrical narrow tip portion 451.

The top portion 450 has spaced transversely directed grooves 452 between which there are transversely circumferentially extending collars 453. The grooves 453 and collars 452 facilitate manual handling of the holder 180.

The flat holder component 127 includes two transversely directed parallel side faces 454 and 455, respectively. These faces 454 and 455 are opposite each other and are joined by end portions 456 and 457. Two circular apertures 458 and 460, respectively, are located within each of the faces 454 and 455. A circular inset 459 is in the face 454 and in the opposite side face 455 there is an opposite circular inset 461. The insets 454 and 460 do not communicate with each other as there is a transverse wall 462 and 463 between them.

The capillary tube 100 passes through the apertures 458 and 460, and the apertures 458 and 460 communicate with both faces 454 and 455. The capillary tube illustrated in FIG. 11 is made by Polymicro Systems Incorporated and has a 25 micron internal diameter and a 150 micron outer diameter. The diameter of the apertures 458 and 460 is in the order of about 0.062 inches. The diameter of insets 459 and 461 is about 0.125 inches. The overall dimensions of holder 180 are thus relatively small.

It is particularly critical to locate capillary tube 100 accurately in its passage through the circular insets 459 and 461. The windows 108 and 109 are formed in the capillary tube 100 in the point of location where the capillary tube 100 passes through the insets 459 and 461. Only a specific energy signal, namely light rays, are to be allowed to pass through the windows 108 and 109, and thus the location of the capillary tube 100 during the injection molding process of component 180 is critical.

Prior to the molding, the capillary tube 100 is held in position in an injection mold. The injection mold has features which can rigidly support the capillary 100 and simultaneously form the apertures 458 and 460. Apertures 458 and 460 extend through the flat face 454 and 455. Since it is not relevant at that location of the flat component 127 whether light passes from one side of face 454 to the other side of face 455 of the holder 180, it is not particularly relevant that a light can pass through the holder 180 at apertures 458 and 460.

Contrarily, insets 459 and 461 are blocked off and apart from each other to prevent penetration of unwanted light from the side of face 454 to the side of face 455. Blocking is effected by two transverse walls 462 and 463, respectively. Each of the walls 462 and 463 have a rectangular cross-section portion 464 and 465, respectively, and a tapered flashing portion 466 and 467. The ends 468 and 469 at the tapered flashing portions 466 and 467, respectively, abut the outside of the capillary tube 100 on opposite sides of the outside wall 104 relative to bore 101. The flashing portions 466 and 467 prevent extraneous stray light from being directed from the side of face 454 to the side of face 455. Such undesirable light may originate from an input fiber optic 119 or an output fiber optic 120 located in adjacency with the insets 459 and 461 or from any other extraneous source.

The flat portions 462 and 463 on the side of face 454 are arranged to receive in abutment the input fiber optic 119 with the end face 305 of the fiber optic input 119 spaced from walls of flats 462 and 463, respectively. The end 151 of a support 571 for the fiber optic input 119 engages the flat sections 462 and 463 and does not engage the tapered portions 466 and 467.

Similarly, on the output side, the ends 151 of the fiber optic support 572 engage the flats 464 and 465 and not the tapered flashing portions 466 and 467. The end face 123 of the output fiber 120 is suitably spaced from the output flats 464 and 465. The sidewalls 470 of each of the insets 459 and 461 act to provide a hollow cylinder effect for the insets 459 and 461, respectively. The walls 420 engage in mating formation with the outside cylindrical wall 471 of the support 571 of the input fiber 119 and outside cylindrical wall 472 of the support 572 of the output fiber 120.

The flat sections 462 and 463 and tapered portions 466 and 467 provide a sturdy means for securing the capillary 100 precisely in its position with the insets 459 and 461. The tapered portions 466 and 467 have engagement ends 468 and 469 which engage with the capillary 100 through the length or diameter of the insets 459 and 461. This also provides an effective seal to extraneous light which would otherwise pass between the insets 459 and 461.

The mold shape used for the injection mold has a feature specifically intended to provide the flashing 464 and 465 with the flat shape portions 462 and 463 and the tapered portions 466 and 467, respectively. This is an intentional use of flashings 464 and 465. Normally flashing is an undesirable characteristic of a molded item and is removed from a molded product. Alternatively, a mold is precision formed to minimize or prevent any degree of flashing. Here, the flashings 464 and 465 are intentionally constructed to provide the secured location of capillary 100.

4. Window Forming

With the capillary 100 so located in holder 180, the windows 108 and 109 can be laser etched into the capillary 100. This is effected by selectively removing the coating 110 selectively from the wall 105 of the capillary tube 100.

An excimer laser effectively provides for the removal of the polyimide coating 110 over the critical dimension to form windows 108 and 109 as required. The laser 500 includes a laser generating source contained within unit 501, a beam direction means 502 to develop a precise beam exiting from an output aperture unit 503.

A computer control system 504 can precisely tailor the beam as required. The laser 500 includes means for illuminating the area where the laser operates so that the precise geometry of the cut can be controlled. The width and length of the windows 108 and 109 can be accurately cut under computer control of the laser 500.

A screen 505 provides visual appearance of the beam directed onto a work platen 506, and a holder 180 located on the platen 506. Viewing ports 507 are provided for microscopically physically viewing the holder 180 and in particular, the capillary 100 located in faces 462 and 463 before and after effecting cutting of windows 108 and 109. Windows 108 and 109 are cut on opposite sides of the capillary 100.

The platen 506 is mounted to be relatively movable on rails 508 and 509 which secures a foundation plate 510 on which the platen 506 is located. The movement on rails 508 and 509 is controlled through the computer 504. The platen 506 includes anchorage means 511 and 512 for securing the holder 180 in position below the aperture unit 503 for the laser beam.

The width 160 of the window 108 is determined in accordance with the optical characteristics and is no greater than the diameter of bore 101 which, as indicated, can have an internal diameter of 25 microns. The laser beam can effect this cut in one or two passes. The depth of the cut should be to remove the coating 110 which is also only several microns in thickness.

The length of the cut along the longitudinal axis of capillary 100 is determined according to the desired length through which light is to pass through the capillary 100. Thus, the length - height 159 of the window 108 can be determined by various characteristics. This can be the diameter of the silicon core 700 of the input fiber 119. This diameter can be about 100 microns. In some situations, the window 108 may have a shorter height 160 than width.

After the window 108 is formed, the window 109 is formed. The characteristics and size of window 109 would be determined according to the optical requirements of the system.

By this technique, accurately shaped and formed windows 108 and 109 are obtained for the capillary 100. The laser processing of the coating 110 forms precise window shapes 108 and 109. The excimer laser 500 is a xenon chloride-based laser operating at a wavelength of 308 nanometers. The short wavelengths makes the laser useful for controlled depth laser cuts. Such a laser cuts 2-3 microns deep per laser shot and, if necessary, as little as 0.2 micron per shot. The laser spot size and shape can be adjusted according to different shapes of the laser beam which are projected through a microscope to the output aperture 503.

The laser used to perform the cutting of windows 108 and 109 is that produced by Florod Corporation of Gardena, Calif. and is Florod Model LFA-308. Other lasers may effectively perform the desired cut, and such lasers may for instance be a Nd-Yag laser.

5. Optical Cavity - Light Envelop (Caustic)

About the wall 105 and coating 110 of the capillary tube 100 at the input window 108, there is formed an input interface 111 which defines the edge of the window 108. Similarly, on the output side about the wall 105 and coating 110, there is formed an output interface 112 which defines the edge about the output window 109. Between the input window 108 and output window 109, there is formed an optical cavity 116 through the capillary tube 100. The refractive index inside bore 101 is $n_2$ and the refractive index of the wall is $n_1$. By forming the optical cavity in this fashion, a critical construction is accurately obtained for detection of a fluid sample through the bore 101.

The bore 101 has a diameter 113 which is shown illustratively as a distance between the optical path as defined by lines 106 and 107. The aperture width or diameter of the windows 108 and 109 is constructed to have a width substantially equal to diameter 113. The windows 108 and 109 may be constructed slightly greater than the diameter 113 to take account of possible inaccuracies in the optical system. However, their width is not substantially greater than the bore diameter 113.

Figure 1:
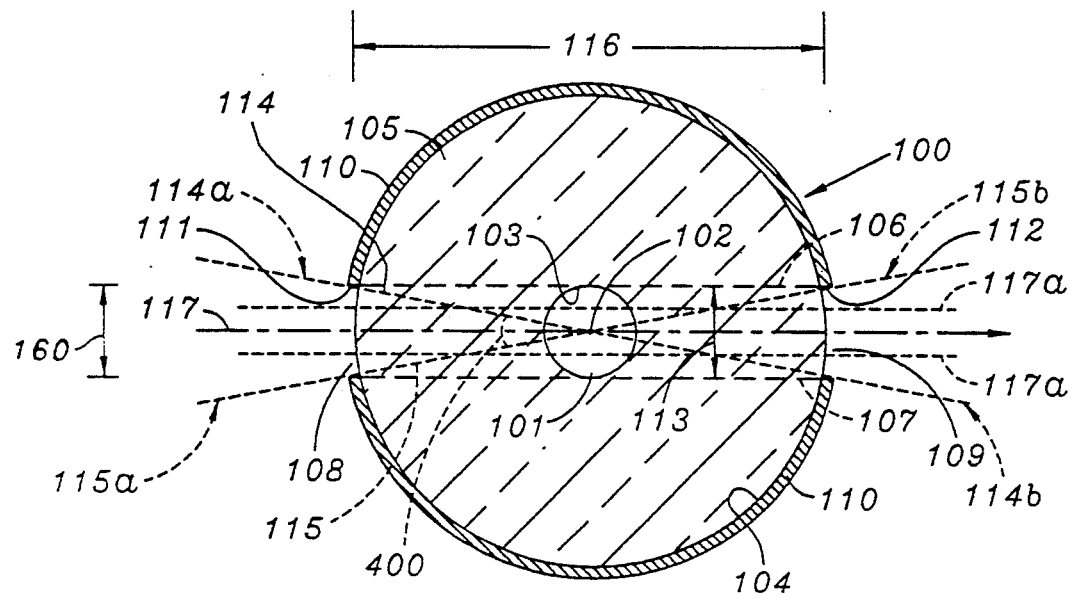
FIG. 1 is a system layout illustrating a cross-sectional end view of a capillary tube with representative light rays passing through the bore of the capillary tube, and diametrically directed lines defining window widths to the capillary tube in terms of the LaGrange Invariant.

Illustrative light rays 114 and 115 are shown in FIGS. 1, 3c and 3d. Should the width size of window 108 or 109 be larger, then light rays would pass into and from the capillary 100 through the quartz wall 105 itself without passing through the bore 101. This is illustrated, for instance, in FIG. 3c, by (imaginary) light rays 206 and 207 parallel to the optical path lines 106 or 107 but outside of the diameter 113 defined by the bore 101. The effect of this is that light rays 206 and 207 would pass through wall 105 and not through the bore 101. This would provide effectively inaccurate detection of the sample through the bore 101. As illustrated, however, in FIG. 3c, the window width 108 and 109 is equal to the diameter 113 of the bore 101 and there would in reality be no light rays 206 and 207. The coating 110 would prevent the generation of rays 206 and 207 in the wall 105.

The optical path lines 106 and 117 are at one cross-sectional level, namely the level of the upper edge of the windows 108 and 109. The windows 108 and 109 have a rectangular cross-section and the lower edge defines parallel optical path lines 106a and 107a. The pairs of optical path lines 106, 107; and lines 106a and 107a define the extremity of the width through which light rays pass through the capillary tube 100. The optical path lines 106, 106a, 107 and 107a form the light envelop or light caustic in the capillary tube 100. The rays 114 and 115 are representative in two dimensions (FIGS. 1 and 3c) of the rays defining parameters of the limiting envelop or caustic of light rays entering and leaving the tube 100. Other rays of light also pass through the bore 101.

The overall envelop or caustic 300 is shown in three dimension and is defined by the bold lines in FIGS. 3d and 6. It commences from the input side and is defined input by optical path lines 301, 302 and 301a and 302a, the path lines 106, 107, 106a and 107a through the capillary tube 100 and the output path lines 303, 304, 303a and 304a exiting the tube 100. The three dimensional perspective arises since the windows 108 and 109 have a height 159. Also, the fiber optic input 119 and fiber optic output 120 have end faces 305 and 306, respectively, with a larger cross-section than the cross-section of the windows 108 and 109. As such, the optic path lines 301, 302, 301a and 302a converge towards the input window 108. The path lines 303, 304, 303a and 304a diverge from the window 109.

The rays 114a and 114b, and 115a and 115b and the three dimensional representations defined by path lines 301, 301a, 302, 302a, 303, 303a, 304 and 304a do not indicate a focusing of light on the center 102. These lines are representative of the light ray slopes from the fiber input 119 to fiber output 120. The cavity between lines 106, 106a, 107 and 107a is a rectangular cubic volume filled with light rays of different slopes and angles emanating from the fiber input 119 and being directed from the input window 108 to the output window 109.

6. LaGrange Invariant

A different manner of defining the width or size of the windows 108 and 109 is by the straight line or ray 114 which passes between the interface 111, through the center 102 of bore 101 and to the opposite interface 112 of the output window 109. Similarly, ray 115 passes between the interface 111 of the input window 108, the bore center 102 and the interface 112 of the output window 109.

A constant in an optical design is the LaGrange Invariant. This constant holds that the energy in an optical system is defined by an angular aperture 400 in the system, and the energy is constant or consistent throughout the system. The angular aperture 400 is limiting for light entering the system. Thus, light from a larger angle would not be able to pass through the optical system, whereas light at any lesser angle would pass through the optical system. The overall optical system is fixed to a value where the LaGrange Invariant for the system is the smallest, namely where the angle is smallest for permitting light passage through the optical system.

With a capillary tube, the optical system is the bore 101, namely it is desirous to pass light energy through the bore 101 over its entire diameter 113. The limiting condition is defined by the maximum angle where the light rays pass through, and only through, the bore 101 across the diameter 113. It is undesirous to have light enter the capillary tube 100 and bypass the bore 101 and reach the detector. Optimally, an opaque mask or coating would be located at the capillary bore surface 103 in a manner to limit the light to the bore 101 only.

Another location for the mask or coating to provide for a limiting aperture is the outside surface 104 of the tube 100. The limiting angular aperture condition is met when the window apertures 108 and 109 are positioned on the opposite sides of outside surface 104 of the bore 101 of the capillary tube 100 and with the aperture widths equal to the diameter 113 of bore 101. The LaGrange Invariant for surface 104 for this configuration derives from the angle defined by a line drawn from the respective interfaces 111 and 112 respectively of opposite sides of the opposing windows 108 and 109. These lines 114 and 115 pass radially through the center 102 of the capillary bore 101.

The LaGrange Invariant for the input and output window apertures 108 and 109 is retained at a relatively low value since, as illustrated in FIG. 1, the tube is relatively thick walled. The value, however, should be as high as possible given other system requirements. This would ensure maximum light energy through the bore 101. The LaGrange Invariant has a value which is substantially consistent through the optical path defined between lines 106 and 107. The value is determined by the substantially maximum angle 400 for receiving light in the bore 101 relative to the substantially least light through the wall 105.

A center line 117 which defines an optical axis through the center 102 of the bore 101 is located midway between the lines 106 and 107 defining the optical path and which pass through interfaces 111 and 112. The window widths 108 and 109 are established by the LaGrange Invariant equation, $H = Yn_1u_0$. Y is half the window width 108 or 109, namely Y, is half the diameter 113. $n_1$ is the refractive index of the silicone quartz wall 105 of the tube 100, and $u_0$ is the angle between the optical axis 117 and either of the rays 114 and 115. $u_0$ is equal to angle 150. H is the LaGrange Invariant, namely the optical constant for the optical cavity as defined by the diameter 116 of the tube 100. H is retained as high as possible to retain the optimal characteristics of the optical system. For the overall optical system, however, the LaGrange Invariant is fixed to a value where the LaGrange Invariant is the smallest possible value of the desired high value.

The value of the LaGrange Invariant is also a function of the diameter 116 of the outside surface 104 relative to the diameter 113 of the capillary bore 101. A larger LaGrange Invariant is realized for a tube having a thin dimension for wall 105. Thus, the effective angle for the light into the bore 101 of a thin wall tube 100 would be greater than for a thick wall tube 100. In FIG. 18b, the greater angle 400 is shown relative to FIG. 18a. Hence, the LaGrange Invariant is greater for the FIG. 18b configuration. Light rays entering the input window 108, but outside the LaGrange Invariant limit, do not pass through the output window 109. This minimizes the stray light contribution to the detected light energy.

As indicated by the diagonal lines passing through the center 102 of the bore 101, the LaGrange Invariant in all illustrations is defined by the smallest aperture in the optical cavity.

6. The Fiber Optic and the Numerical Aperture

The fiber optic conductors 119 and 120, if adequately illuminated, contain light energy at all angles within the Numerical Aperture of the optic fibers 119 and 120. This is a function of the difference in the refractive index of the core material 121 and the cladding material 122. Typical values for the Numerical Aperture for fused silica optical fibers is 0.22. This value defines an angular cone with an angle 150 of about 15 degree half angle. Each half angle 150 is illustrated in FIGS. 3a, 3b, 3c, and 18a to 18g.

As illustrated in FIG. 3c, the half angle 150 is also the half angle of a cone of light centered about the axis 401 of the optical fiber input 119. As the rays of light 402 and 403 leave the end face 305 of the fiber input 119 at the interface between the core 121 and cladding 122, there are diverging lines 402 and 403 which are directed to the outside surface of the polyimide coating 110. Such light rays do not enter the wall 105 of the tube 100. There are also reflected rays 404 and 405 at angle 150 which are coincident with input envelop rays 114a and 115a, respectively, as illustrated in FIG. 1. All rays from the face 305 emanating from points 406 and 407 which have an angle less than the angle 150 will pass through the input window 108, the bore 101 and out of the output window 109. Since there are no rays from points 406 and 407 having a greater angle because of the Numerical Aperture limitation, the tube 100 is not subject to unnecessary light which would have passed through the bore 101 and/or wall 105 and not reach the output window 109.

Between the interface points 406 and 407 being at the interface between core 121 and cladding 122 on the face 305, light rays 408 will emanate as indicated in all directions, but within the angle determined by the Numerical Aperture of the fiber optic input 119. All the light rays in the conical envelop 700 will enter the input window 108 and pass through the wall 105. Depending on the angle, some of the light rays in envelop 700 also pass through the bore 101. If aligned correctly, some of the light rays, for instance rays 410, also exit the output window 105 and enter the fiber optic output 120. In FIG. 3c, representative rays 408, 409 and 410 are illustrated being emitted from face 305. Rays 408 and 409 do not pass through output window 109.

The receiving face 306 of output fiber optic 120 receives light according to its Numerical Aperture. The angle 150 is applicable also to the fiber optic output 120. In FIG. 3c, the representative rays in the conical envelop 411 are shown as the light rays which would normally be received. As illustrated, from the interface points 412 and 413 between core 121 and cladding 122 of face 306, the fiber optic 120 would receive light from a diverging source 414 and converging source 415.

Light falling outside the area defined by rays 114b and 115b would not be received in practice, because there is no real light from source 117 since the coating 110 has blocked the light rays. Inside the area bounded by the rays 114b and 115b, light at angles less than angle 150 are received. Representative rays 416, 417 and 418 are illustrated. Such light received on face 306 has passed directly through window 108, wall 105, bore 101, wall 105 and window 109. The width of window 108, as well as the Numerical Aperture of output fiber 120, limits the area from which light can be received by face 306. Light at the interface points 412 and 413 which does enter the fiber optics output 120 is stray light from the area around the tube 100.

The fiber optic input 119 and output 120 have a diameter for the core 121 of between 200 microns and 300 microns. The diameter of the outer cladding 122 is between 220 to 330 microns, respectively. A buffer coating 600 is applied about the cladding 122. In their respective situations, the diameter of the buffer coating is between 240 and 360 microns.

The fiber optics 119 and 120 are produced by Polymicro Technologies, Inc. of Phoenix, Ariz. and is of the series where the transmission is between 180 to 1100 nanometers. The core has a high OH⁻. The material of core 121 is made of silica, the material cladding 122 is a doped-silica and the buffer coating 600 is either acrylate, silicon or polyimide buffer.

7. Matching Fiber Optics and Optical System

In matching fiber optic input 119 and fiber optic output 120 relative to the optical system, the configuration is established with a slightly higher value of the LaGrange Invariant (H) in the source 117 and detector 118 so as to compensate for any mechanical imperfection in the match of the alignment.

Figure 2:
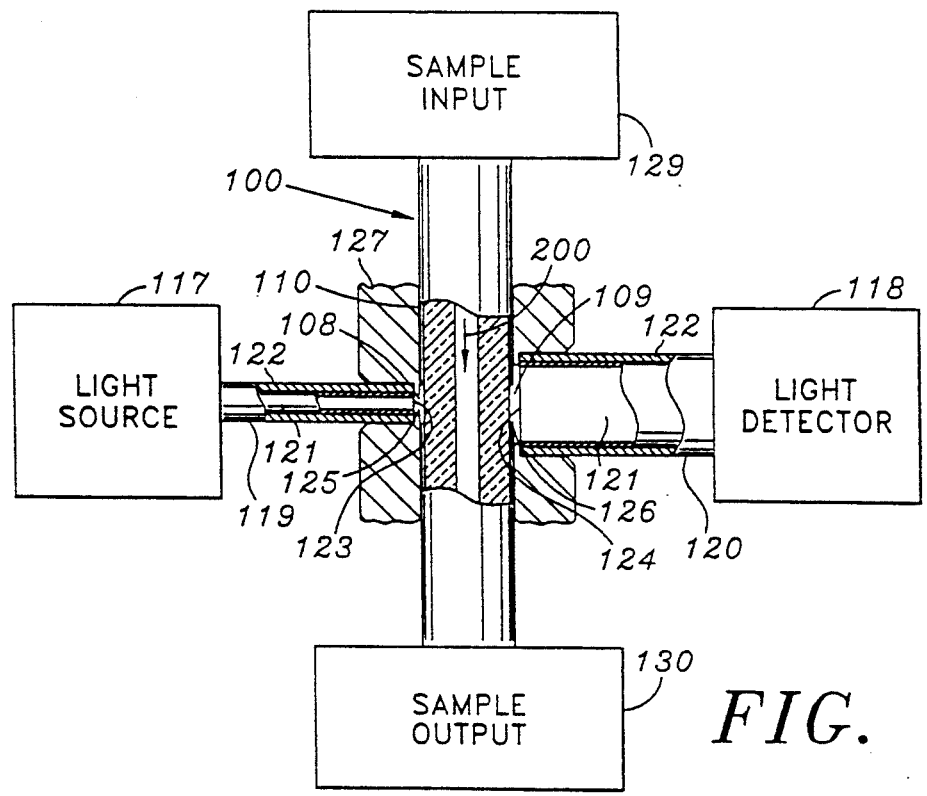
FIG. 2 is a partial diagrammatic side view, partly in section, of a capillary electrophoresis optical system with an input fiber, output fiber, sample input and sample output.

In FIG. 2, a source 117 for laser light and a detector 118 for the laser light after passage through the capillary tube 100 are diagrammatically illustrated. The source 117 is connected with the fiber optic input conductor 119, and the detector 118 is connected with a fiber optic output conductor 120. The diameter of the fiber optic output 120 is larger than the fiber optic input 119. The fiber optic input 119 and output 120 are suitably located by means of fiber optic supports 151 located relative to the input window 108 and output window 109. The supports 151 form part of the fiber optic input and output mechanisms 571 and 572, respectively.

The supports 151 are located in abutment within circular insets 459 and 461 associated with the holder 180.

By placing the optical fiber 119 with the end 123 of the holding mechanism 571 in close proximity to the input window 108 of the capillary tube 108, the energy propagated into the capillary tube 100 fills all possible ray directions within the LaGrange Invariant defined above. By placing the optical fiber output 120 with the end 124 of mechanism 572 in close proximity to the output window 109, all exiting energy from the window 109 fulfilling the LaGrange Invariant is captured for transmission to the active surface of the detector 118. The optical fiber input and output conductors 119 and 120 are slightly larger than the dimensions of windows 108 and 109.

The fibers 119 and 120 are positioning in the holder 180 which locates the relative positions of the fiber ends 123 and 124 and the capillary tube 100 in an optimal configuration within reasonable manufacturable tolerance limits.

The distance 125 between the end face 305 of input optic fiber input 119 and input window 108 is configured so that the operative light leaving from the end face 305 is of a slightly larger, but similar cross-section to the window aperture 108. The output of light from the face 305 is in the form of an angular diverging circular cone 161 (FIGS. 3b and 6). The light, however, that passes into input window 108 is a rectangular shape. There is an optical envelop or caustic converging conical shape 153 that has its apex directed towards the center 102 of the bore 101. The input optical caustic 153 is part of the overall caustic 300.

In this manner, the light from the fiber optic input 119 is matched to the window 108 so that optimal light energy passes into the optical path through the capillary bore 101.

The rectangular converging conical shape caustic 153 is shown in two dimensions defined by lines 154 and 155 (FIG. 3a) and is shown in three dimensions by lines 301, 302, 301a and 302a (FIG. 3d). The caustic is defined about an angle 152 between each of respective lines 154 and 155 and axis 156 through center 102. The angle 152 is substantially equal to the angle 150 for the Numerical Aperture of the fiber 119. Collectively, both of angles 152 to either side of axis 156 is equal to angle 400.

On the output side, the end face 306 is spaced from the window 109 by a distance 126. In this manner, the rectangular shape of light is included in an optical envelop being a diverging caustic cone 170 defined between lines 157 and 158. The light impacts the effective receiving area of face 306 of the fiber output 120 with a cross-section smaller than the cross-section to the core material 121 of the output fiber 120. The diverging caustic cone 170 from the output window 109 has its apex directed towards the center 102 of the bore 101.

The light travels within diverging caustic cone 170 downstream from face 306. The caustic portion 170 is part of the envelop 300. The caustic or envelop 170 is thus composed of two sections which are a first portion between the window 109 and the face 306, and a second portion between the face 306 and a distance inside the fiber 120 where the core 121 meets the cladding 122.

The fiber optic conductors 119 and 120 transmit an optical beam with a large degree of integrity within the Numerical Aperture. Light within this Aperture is transmitted into the optical cavity defined by diameter 116 and between lines 106, 107, 106a and 107a within the capillary 100. The light envelop 300 in the capillary 100 is in the shape of a cube 420. The components of light envelop 300 are thus the input converging rectangular cone 153, cube 420 through the capillary tube and the diverging rectangular cone 170 from the output window 109. This envelop 300 is filled with light from the fiber input 119 which light traverses the bore 101 and is then communicated to fiber output 120.

With this arrangement, the windows 108 and 109 are rectangular in shape. The height-length 159 of the window 108 is defined by the diameter of the core 121 of fiber optic 119. The width 160 of the window 108 is defined by the diameter 113 of the bore 101 of capillary tube 100. The Window 108 defines and limits the shape of the converging cone 153 of light input into the capillary 100. Outside the capillary tube 100 and upstream the input window 108, the diverging cone is regular and circular as shown by 161. It is, however, light from only the rectangular portion 261 on face 305 that enters the window 108 in a manner to later exit window 109. Inside the capillary 100, the envelop is like a rectangular cube limited by the window 108. The output converging cone 170 is also limited to the rectangular sliced appearance both while inside the capillary and exiting the window 109 and entering fiber optic output 120. The light fills the entire optical path along the optical cavity 116 as defined between lines 106, 106a, 107 and 107a. Thus, for instance, light rays 117a parallel to the axis 117 also pass through the optical cavity (FIG. 1) path as limited by the diameter 113. Other exemplary rays 117b and 117c are shown in the light envelop 300 (FIG. 3d).

The light envelop 300 showing light into, in and from the optical cavity 116 is also illustrated in FIGS. 3d and 6. The diverging circular conical caustic 161 is upstream the input window 108. The rectangular cubic caustic 400 of light is shown downstream the input window 108. The conical converging caustic 153 are directed from the face 305 to the window 108 towards the center 102. Also shown in FIGS. 3d and 6 is an imaginary window 181 at the input face 306 of core 121 of the output fiber 120. Light travels into the output fibre core 121 and impacts the perimeter of core 121 in a rectangular manner 182.

Light outside of the Numerical Aperture does not enter the optical cavity 116. Also, light within the Numerical Aperture and directed onto the opaque coating 110 does not enter the optical cavity 116 through the input window 108. By making the optical fiber output 120 larger than the diameter of the optical fiber input 119, the entire light envelop 153 is received at the fiber output 120.

By accurately setting up the relationship of the input fiber 119 at its end face 305 relative to input window 108, and the output fiber 120 at its end face 306 relative to output window 109, the effects of stray light are reduced. This is illustrated in FIGS. 3a, 6 and 113. In FIGS. 3a and 13, there is illustrated the manner in which the flashings 466 and 467 to either side of the windows 108 and 119 prevents light from the input fiber 109 passing past the capillary tube 100 to the output side or the fiber output 120. The flashings 466 and 467 extends along the length of the capillary tube 100 in insets 459 and 461.

Similarly, the effect of scattered light, refraction, reflection and other undesirable optical phenomena are reduced. The optical system affords control of the optical pathlength and structure of the optical path and the avoidance of stray light and reduction of interference scatter.

8. Fiber Optic Anchorage

The holder 180 is located positively with end 151 for the fiber optic input 119 and end 151 for the fiber optic output 120. The portion 127 of holder 180 is contained within a vertical support structure 601 and 602. The support structure includes transverse extending arms 650 and 651 with threads 603 and 604 on the outside. Nut configurations 605 and 606 are respectively located with the threaded portions 603 and 604. The nuts 605 and 606 include axial apertures 607 and 608, respectively, through which holder mechanisms 571 and 572 for the fiber optic input 119 and the fiber optic output 120 are respectively located.

The nut constructions 605 and 606 are threaded along threads 603 and 604, respectively, so as to firmly and accurately secure the fiber optic holder mechanisms 571 and 572 in adjacent relationship accurately within the circular insets 459 and 461, respectively.

The downstream portion 451 of the holder 180 is located in a seal 609. The leading end output tip has a spherical end 610 which directs the output 611 of the capillary tube 100 into a manifold channel 612.

9. Electrophoretic Operation and Results

The force for moving fluid between the sample input 129 and sample output 130 is provided by establishing an appropriate voltage between the sample input 129 and sample output 130. Such voltage would extend down the sample fluid passing through the capillary 100. It causes the electrophoresis migration of sample through the capillary 100. As the sample passes past the windows 108 and 109, it is exposed to light from the light source 117 which is directed along the optical path as defined. This light is received by the light detector 118 from which an analysis of the sample passing through the bore 101 can be effected.

The configuration of the capillary electrophoresis of optical system provides for optimal optical detection without interference. Maximal light from the light source 117 is passed through the sample in the bore 101 without interference from peripheral and surrounding areas and the maximal signal is received by the detector 118.

Noticeably improved data are obtained in that the there is an efficient usage of light generated from the fiber optic input 119 through the bore 101 to the fiber optic output 120 with the minimal of stray light effects. Typical data are set out in FIG. 20a and 20b. Comparative data with a prior art capillary electrophoresis system would require the generation of substantially more light from the fiber optic input. Substantially far more complex and bulky equipment is necessary to eliminate undesirable light effects on the system. The analytic results with the present invention are more detailed and informative than prior art systems, and can be obtained in significantly less time than prior art systems and with greater accuracy and efficiency.

10. Miscellaneous

The configuration of the envelop 300 maximizes the amount of light from a given source of light through the sample in bore 101. Effectively this is achieved without additional optical elements such as the focusing devices or slits which can cause aberrations to the light. The windows 108 and 109 effectively act as the aperture for the light and by ensuring compliance with the LaGrange Invariant, effective maximal efficiency of light from the light source is obtained in the tube 100 and through the bore 101 with the minimum of stray light and aberrated light. There is no "air-slit-air-glass" passage of the light with consequence multiple distortions. There is only an "air-glass" passage with consequently significantly less distortion.

As illustrated in FIG. 12, the height of window 108 is larger than the width. Different constructions of the window are possible. In FIG. 16, a window of relatively broader width and a shorter height is illustrated.

In FIGS. 17a through 17e, different cross-sections of capillary tube 100 are illustrated. The bore 101 is shown as circular. Situations, however, can arise where the bore 101 is of a different cross-section. The cross-section of the bore is different.

In FIG. 17a, the input window 108 is on a curved surface as is the output window 108. The faces of the capillary tube 100 which are not adjacent the input windows, namely faces 602 and 603, are flat. The other than the curved faces 604 and 605 and the capillary cross-section is substantially square. The coating 110 is formed on the outer faces 602, 603 and 605 as required.

In FIG. 17b, a similar structure to FIG. 17a is disclosed. The shape of the capillary, however, is relatively more squat in that the length of the side 604 and 605 is relatively shorter than the sides 602 and 603. In FIG. 17c, the sides 604 and 605 are relatively larger than the sides 602 and 603. In FIG. 17d, a square capillary cross-section is shown with sides 602 and 603 straight and sides 604 and 605 also straight.

In the configuration illustrated in FIG. 17e, the windows 108 and 109 are formed by removing not only part of the coating 110 but a portion of the wall thickness 105. The sides 606 and 607 of the input window slope convergingly towards the bore 101. The inside face or inside side 608 of the window is curved to conform with a center 102 for the bore 101. Similarly, the output window has a diverging side 609 and 610 which form sidewalls to the output window 109. Face 611 is a face cut into the wall thickness 105. The face 611 has a curvature to conform with a center 102. The construction illustrated in FIG. 17e is set up to insure that the inside of the windows are as close to the wall as possible thereby increasing the value of the LaGrange Invariant of the system. The walls 606 and 607 of window 108, and the walls 609 and 610 of window 109 are sloped so as to conform with the angular relationship as would be established by rays 114a, 115a, 114b and 115b, respectively.

Other shapes of the capillary tube are possible, for instance the shape can be triangular or any other suitable geometric shape. One of other of windows 108 or 109 can be cut into the wall thickness 105 to different selected depths as may be required by the system.

In the different representations of FIGS. 18a to 18g, the windows 108 and 109 are shown defined differently relatively to the bore 110 of different diameters and with different degrees of coating removal.

The LaGrange Invariant is related to the thickness of wall 105. The thicker the wall 105, the lower is the H value. The thinner the wall 105, the higher is the H value. Should the wall 105 be very thin, then the fiber optic end face 305 defines the LaGrange limit.

The relationship of different thickness tubes 100 is illustrated in FIGS. 18a through 18g with respect to the fiber input 119 and fiber output 120. The light envelop is two-dimensions is shown by the bold lines.

Figure 18A:
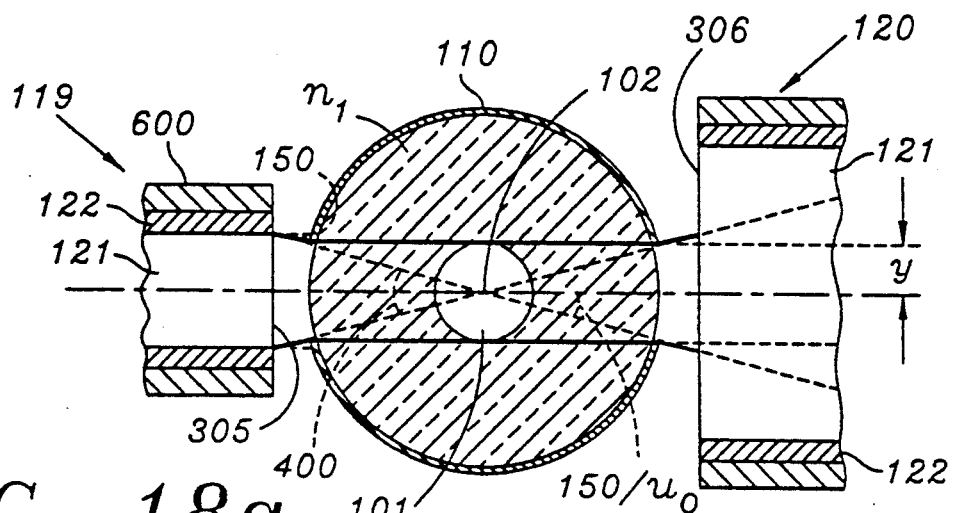
Figure 18B:
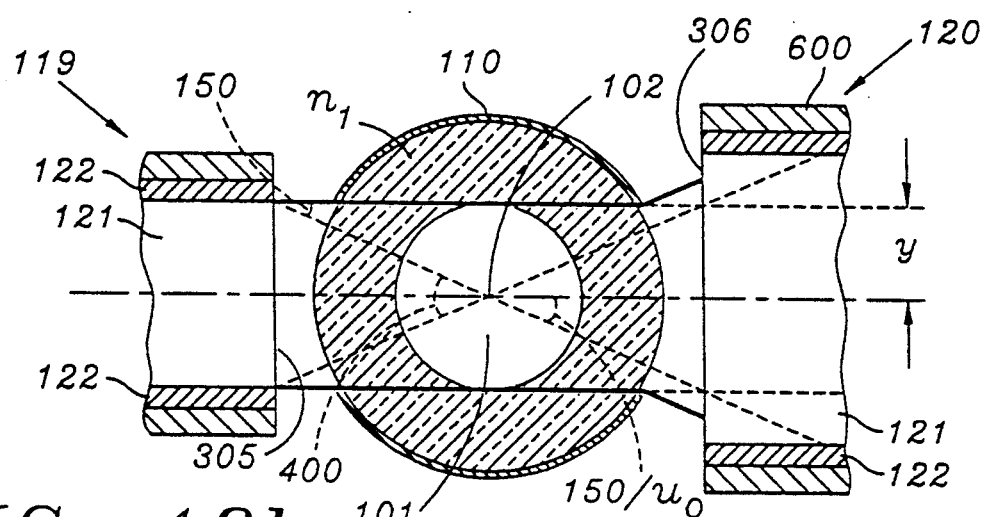
Figure 18C:
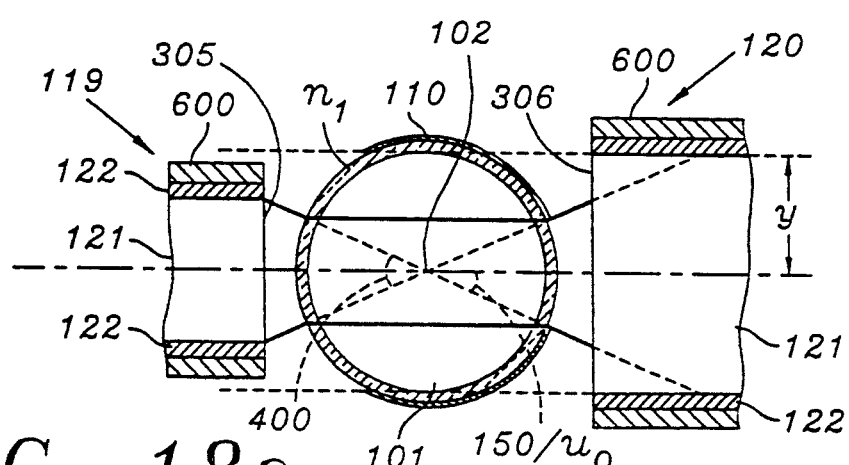

The LaGrange Invariant illustrated is smaller in FIG. 18a and larger in FIG. 18b. In FIG. 18f, the LaGrange Invariant is determined by the fiber optic input and output and faces 305 and 306.

Figure 18D:
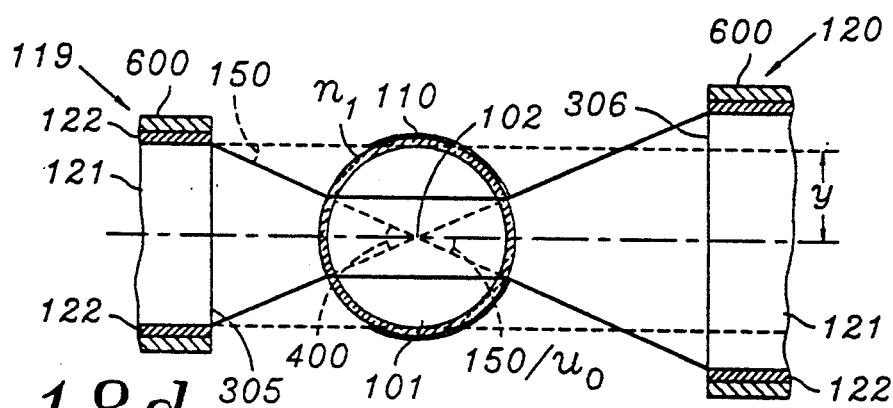

In FIG. 18d, a larger fiber input 119 and fiber output 120 are employed. The end faces 305 and 306 are relatively further removed from windows 108 and 109. In FIG. 18d, the input window is no greater than the diameter 113. By removing the end faces 305 and 306 from the capillary tube 100, it is possible that more extraneous light will enter the tube.

In FIG. 18c, the capillary tube 100 construction is similar to FIG. 18d; however, a smaller diameter fiber input 119 and fiber output 120 are employed. The envelops show that not all of the input signal bore is illuminated by the input signal.

In FIG. 18d, the output window 109 is not greater than the bore 101. A large fiber input 1119 is provided, the fiber input 119 being further removed from the capillary 100. Alternatively, a smaller fiber input 119 located closer to the capillary 100 can be used. The envelop shows that not all of the bore is illuminated by the input signal.

In FIG. 18f, both the input window 108 and output window 109 are not greater than the bore 101. Not all of the bore 101 is illuminated by the input signal.

In all the illustrations in each of FIGS. 18a to 18g, the Numerical Aperture is assumed to be the same for fiber input 119 and fiber output 120.

With the holder-capillary-window structure accurately established, other components of the optical system can be constituted and aligned with the capillary tube 100 with greater tolerances. Since the holder 180 secures the capillary tube 100 in fixed relationship, and the windows 108 and 109 are pre-formed accurately in the tube 100, there is no possibility of relative movement between the windows 108 and 109 and the bore 101.

The holder 180 is then fixed in its support in an electrophoresis system and only the input and output fiber optics 119 and 120, respectively, then have to be physically and optically aligned with the holder 180. The "de-coupling" of the physical alignment relationship of the windows 108 and 109 and capillary tube 100 on the one hand from the fiber optics 119 and 120 on the other hand, simplifies the alignment of the system. The electrophoresis system is a significant improvement over prior art systems which had multiple optical components to align. The holder 180 and fiber optic input 119 and output 120 are relatively larger components than the windows themselves and hence, there is greater ease of alignment.

Many more examples of the invention exist, each differing from the other in matters of detail only.

Different kinds of signal source and detectors can be used. Detection to sense the separated components in the capillary bore can include, selectively, conductivity detectors, radioactivity detectors and various optical techniques such as absorbance, fluorescence, refractive index gradients and light scatter detectors.

Although the detected signal has been described for particular wavelengths, it is apparent that the electrophoresis system could operate at many different wavelengths. Signals at multiple discrete wavelengths can be applied to one or more detection paths applied to the tube. Such range of wavelengths could be limited or extensive in the electromagnetic spectrum, so long as the masking constituting the window widths suitably excludes the signal at the selected wavelength from passing through undesirable sections of the tube wall.

Although the system has been described with reference to a single capillary electrophoresis unit, it is clear that multiple systems can be used in series or tandem to provide for a continuous monitoring process. This is illustrated in FIG. 7. Thus, different input fibers 109, and output fibers 120 can be fed to a multiple series of capillary tubes 100 aligned, for instance, on a turntable. A single light source 117 and a single light detector 118 can be used in sequence or simultaneously for the electrophoresis system, with each capillary tube 100 held in their respective fiber optic holder 180 through the holder component 127. Sample inputs 129 and outputs 130 can be provided as necessary.

As illustrated in FIG. 7, there are a series of multiple optic fiber inputs 119 and multiple outputs 120 along the longitudinal length of multiple capillary tubes 100. In this manner, the travel of different samples 200 down the bore 101 of different tubes 100 can be monitored as desired.

In the arrangement of FIG. 8, there is located a scanning light source 217 as the input and a linear array detector 218 as the detection means. The windows 208 and 209 in these capillary tubes 100 are longitudinally extended to be greater in the length associated with the optical fiber diameter size of core 121. The light source 217 has input window 223 and the detector 224 has receiving window 218.

In other situations it is possible to have multiple input windows and output windows arranged angularly around the central axis of the capillary tube at selective angles. In different situations input light of different selected wavelengths can be input into the capillary tube through selected input windows about the axis. Different output windows would then receive the light with the pertinent information about the sample in the tube 100.

Figure 18E:
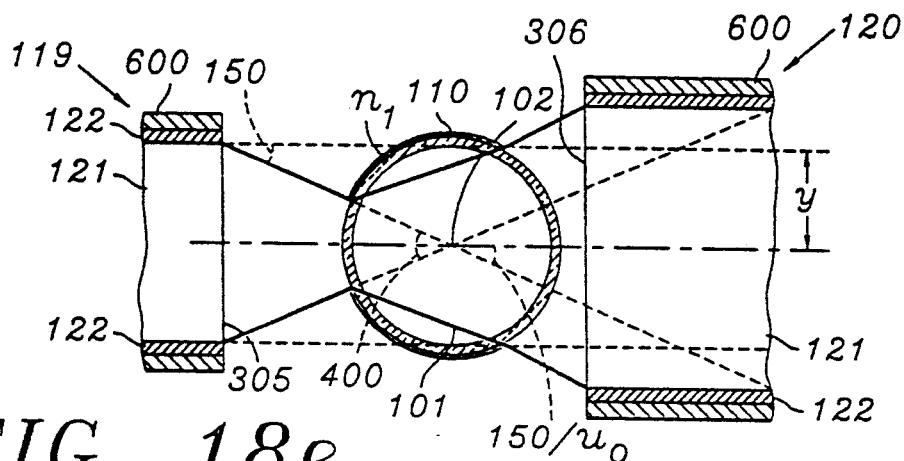
Figure 18F:
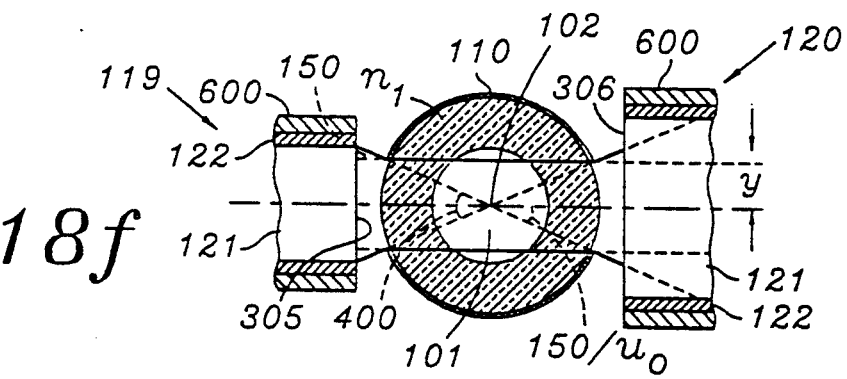
Figure 18G:
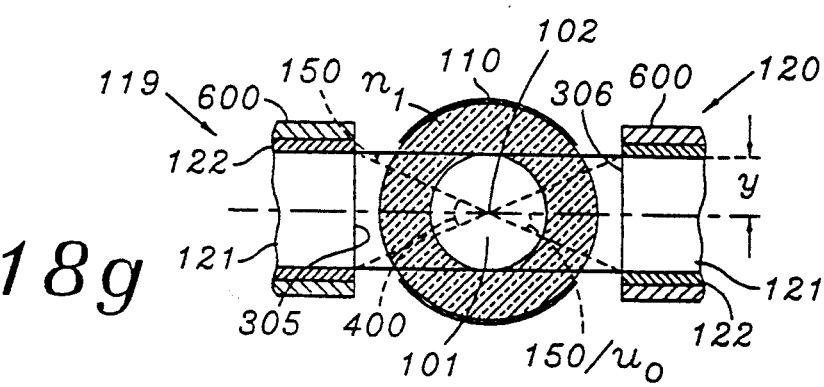

The construction illustrated in FIGS. 1 through 6 is one where both windows 108 and 109 have an aperture width 160 substantially equal to the diameter 113 of bore 101. In some situations, only one of the apertures 108 or 109 may be equal to the bore diameter 113, for instance, as illustrated in FIGS. 18c, 18d and 18e. The preferable construction has both window apertures 108 and 109 with a width 160 equal to the diameter 113. As illustrated in FIG. 5, the height 159 of the apertures 108 and 109 is greater than the width 160.

Also, in other situations the input window and/or output window may be defined by the output face of the fiber optic input and the receiving face of the fiber optic output. Thus, where the width of face 305 or 306 is substantially less than or no greater than the bore of the capillary, substantially the same effect may be achieved as having the window defined by the surface coating 110 of the capillary tube 100.

In some cases where the window 108 or 109 is of a lesser width than the diameter of bore 101, the amount of light passing into the bore 101 and from the bore 101 would be less than maximally possible within the sense of the invention. This is shown in FIG. 18f. The information detected and obtained from the electrophoresis system may nonetheless be sufficient and still superior to prior art systems.

Situations could also exist where only one window 108 or 109 is substantially equal or no greater than the diameter of bore 101, and the other window 108 or 109 is greater than the bore diameter. In this case the smallest window width would govern the range of light passing from the input fiber through the tube and bore and into the output fiber.

This case could be applicable whether the window 108 or 109 is considered as being on the face of the fiber or one the surface of the tube.

In different cases, the relative widths of the input and output windows are different. Thus, the envelop through the bore need not be a regular cubic shape, but tapers between the two windows. This is shown in FIG. 18e.

The shape of the windows 108 and 109 have been described as essentially rectangular about the periphery of the capillary tube 100. The rectangle is essentially parallel to the bore. In some cases, the perimeter or edge of the windows may be curved. In this event, the width of the windows is considered as the broadest or average width of the window. In other cases, the line of the windows may be non-parallel to the bore.

The invention is to be considered in terms of the following claims.

We claim:

1. A capillary electrophoresis system comprising a capillary tube having a bore, an inner surface defining the bore, an outer surface, and a wall thickness of the tube defined between the surfaces, the bore having a width and being for transporting fluid, an input window in an outer surface portion of the tube and an output window in an outer surface portion of the tube, the input window and output window being spaced apart, at least one of the input window or output window defining a window width, and wherein the window width is not substantially greater than the bore width.

2. A system as claimed in claim 1 wherein the width of both the windows are not greater than the bore width.

3. A system as claimed in claim 1 wherein the width of at least one of the windows is equal to the bore width.

4. A system as claimed in claim 3 wherein the width of both the windows is equal to the bore width.

5. A capillary electrophoresis system comprising a capillary tube having a bore, the bore having a center, an inner surface defining the bore with a selected diameter, an outer surface, a wall thickness of the tube being defined between the surfaces, the bore being for transporting fluid past a detection path, an input window on an outer surface portion of the bore, the input window having opposite interfaces with the surface thereby defining the input window width, and an output window on an opposite outer surface portion of the tube, the output window having opposite interfaces with the surface thereby defining the output window width, and wherein the input and output window widths are additionally defined by a pair of intersecting straight lines directed from each respective opposite interface of an input window radially through the center of the bore to each respective opposite interface of the output window, and wherein the intersecting lines define a LaGrange Invariant for the detection path.

6. A capillary electrophoresis system comprising a capillary tube having a bore, an inner surface defining the bore with a selected diameter, an outer surface, a wall thickness of the tube being defined between the surfaces, the bore being for transporting fluid past a detection path, an input window on an outer surface portion of the tube and an output window on an opposite outer surface portion of the tube, wherein the input window and the output window define respective widths, the detection path being defined between the input window through the bore and to the output window, and wherein there is a LaGrange Invariant for the detection path and wherein the input and output windows have a width such that the LaGrange Invariant is substantially consistent through the detection path.

7. A system as claimed in claim 6 wherein the LaGrange Invariant is determined by the substantially maximum angle for receiving a signal in the bore relative to the substantially least signal through the tube wall.

8. A system as claimed in claim 7 wherein the LaGrange Invariant is selected to be the substantially highest value for the detection path.

9. A capillary electrophoresis system comprising a capillary tube having a bore, the bore having a center, an inner surface defining the bore with a selected diameter, an outer surface, a wall thickness of the tube being defined between the surfaces, the bore being for transporting fluid past a detection path, an input window on an outer surface portion of the tube, the input window having opposite interfaces with the outer surface of the tube thereby defining the input window width, and an output window on an opposite outer surface portion of the bore, the output window having opposite interfaces with the outer surface of the tube thereby defining the output window width, an axis through the center of the bore and a position midway between the interfaces of the input window and midway between the interfaces of the output window, and wherein the input and output window widths are established by $H = Yn_1u_0$ wherein Y is substantially half the window widths and substantially half the diameter of the bore, $n_1$ is the refractive index of the tube, $u_0$ is the angle between the axis and the line from an interface of the windows through the center, and H is an optical constant for the system.

10. A system as claimed in claim 1 including an fiber optic input for directing input light to the input window, the fiber optic input having a Numerical Aperture and wherein the fiber optic input includes a core having an end face spaced a distance from the input window whereby light is transmitted from the fiber optic input end face, the end face having an interface and wherein lines of light from the interface are directed at a converging angle substantially equal to a half angle for the Numerical Aperture, and wherein the converging lines of light are directed towards the input window at a location defining a width substantially equal to the window width.

11. A system as claimed in claim 10 wherein the lines of light at the half angle for a Numerical Aperture of the fiber are directed towards a center of the bore.

12. A system as claimed in claim 10 including a fiber optic output for receiving light from the output window.

13. A system as claimed in claim 1 including an fiber optic output for receiving light from the output window, and the fiber optic output having a Numerical Aperture, and wherein the fiber optic output includes a core having an output end face spaced a distance from the output window, the end face having an interface with a cladding and wherein output lines of light from the output window define a diverging angle related to the Numerical Aperture, the diverging angle of light from the interface of the output window impacting the output fiber, such lines defining a width at the end face at least substantially no wider than the width of the end face of the fiber optic output.

14. A system as claimed in claim 13 wherein the diverging lines of light emanate from a center of the bore.

15. A system as claimed in claim 1 wherein the capillary tube includes a coating and the windows are formed by selective removal of the coating.

16. A system as claimed in claim 5 wherein the capillary tube includes a coating and the windows are formed by selective removal of the coating.

17. A system as claimed in claim 6 wherein the capillary tube includes a coating and the windows are formed by selective removal of the coating.

18. A system as claimed in claim 9 wherein the capillary tube includes a coating and the windows are formed by selective removal of the coating.

19. A system as claimed in claim 10 wherein the capillary tube includes a coating and the windows are formed by selective removal of the coating.

20. A system as claimed in claim 13 wherein the capillary tube includes a coating and the windows are formed by selective removal of the coating.

21. A system as claimed in claim 1 including multiple input windows spaced from each other and multiple output windows, the windows being spaced from each other.

22. A system as claimed in claim 1 wherein the input window is located opposite the output window.

23. A system as claimed in claim 21 wherein respective input windows are related to opposite output windows.

24. A system as claimed in claim 1 wherein the windows have a rectangular cross-section.

25. A capillary electrophoresis system comprising a capillary tube having a bore, an inner surface defining the bore diameter, an outer surface, a wall thickness of the tube being defined between the surfaces, the bore being for transporting fluid past a detection path, an input window on an outer surface portion of the tube and an output window on an opposite outer surface portion of the tube, at least one of the input window and output window defining a width, the width being substantially equal to the bore diameter, means for generating a signal, and wherein the signal directed along the detection path between the input and output windows essentially does not pass through the wall without additionally passing through the bore.

26. A system as claimed in claim 25 including a fiber optic input having a core and cladding for directing input light to the input window, and wherein the fiber optic input includes an end face for the core, the end face being spaced a distance from the input window whereby light related to a Numerical Aperture of the fiber optic input from an interface of the core and cladding defines a substantially straight line adjacent an edge of the input window width and to the center of the bore.

27. A system as claimed in claim 25 including a fiber optic output including a core and cladding for receiving output light from the output window, and wherein the fiber optic output includes an end face for the core, the end face being spaced a distance from the output window whereby output light related to a Numerical Aperture of the fiber optic output directed along a substantially straight line from the center of the bore adjacent an edge of the output window width is directed to a position at least within the interface of the core and cladding.

28. A system as claimed in claim 26 including a fiber optic output including a core and cladding for receiving output light from the output window, and wherein the fiber optic output includes an end face for the core, the end face being spaced a distance from the output window whereby the light from the center of the bore directed adjacent an edge of the output window width is directed to a position at least within the interface of the core and cladding.

29. A capillary electrophoresis optical system comprising a capillary tube having a bore with a center, an inner surface defining the bore with a selected diameter, an outer surface, and a wall thickness of the tube defined between the surfaces, the bore being for transporting fluid past an optical path, an optical input window in an outer surface of the tube and an optical output window in an opposite outer surface portion of the tube, at least one of the input window or output window defining an aperture width, and wherein the window width is not substantially greater than the bore diameter.

30. A system as claimed in claim 29 wherein the width of both the windows are not greater than the bore diameter.

31. A system as claimed in claim 29 wherein the width of at least one of the windows is equal to the bore diameter.

32. A system as claimed in claim 31 wherein the width of both the windows is equal to the bore diameter.

33. A capillary electrophoresis optical system comprising a capillary tube having a bore, the bore having a center, an inner surface defining the bore with a selected diameter, an outer surface, a wall thickness of the tube being defined between the surface, the bore being for transporting fluid past an optical path, an optical input window on an outer surface portion of the bore, the input window having opposite interfaces with the surface thereby defining the input window width, and an optical output window on an opposite outer surface portion of the tube, the output window having opposite interfaces with the surface thereby defining the output window width, and wherein the input and output window widths are defined by a pair of intersecting straight lines directed from each respective opposite interface of an input window radially through the center of the bore to each respective opposite interface of the output window and the window widths are substantially equal to the bore diameter.

34. A capillary electrophoresis optical system comprising a capillary tube having a bore, an inner surface defining the bore with a selected diameter, an outer surface, a wall thickness of the tube being defined between the surfaces, the bore being for transporting fluid past an optical path, an optical input window on an outer surface portion of the tube and an optical output window on an opposite outer surface portion of the tube, wherein the input window and the output window define respective widths, the optical path being defined between the input window and output window and wherein there is a LaGrange Invariant for the optical path and wherein the LaGrange Invariant is substantially consistent through the optical path.

35. A system as claimed in claim 34 wherein the LaGrange Invariant is determined by the substantially maximum angle for receiving light in the bore relative to the substantially least light through the tube wall.

36. A system as claimed in claim 35 wherein the LaGrange Invariant is selected to be substantially the highest value for the optical path.

37. A capillary electrophoresis optical system comprising a capillary tube having a bore, the bore having a center, an inner surface defining the bore with a selected diameter, an outer surface, a wall thickness of the tube being defined between the surfaces, the bore being for transporting fluid past an optical path, an optical input window on an outer surface portion of the tube, the input window having opposite interfaces with the outer surface of the tube thereby defining the input window width, and an optical output window on an opposite outer surface portion of the bore, the output window having opposite interfaces with the outer surface of the tube thereby defining the output window width, an optical axis through the center of the bore and a position midway between the interfaces of input window and midway between the interfaces of the output window, and wherein the input and output window widths are established by $H = Y n_1 u_0$ wherein Y is substantially half the window widths and substantially half the diameter of the bore, $n_1$ is the refractive index of the tube, $u_0$ is the angle between the optical axis and the line from an interface of the windows through the center, and H is an optical constant for the system.

38. A system as claimed in claim 29 including a fiber optic input for directing input light to the input window, the fiber optic input having a Numerical Aperture, and wherein the fiber optic input includes a core having an end face spaced a distance from the input window whereby light is transmitted from the fiber optic input end face, the end face having an interface with a cladding and wherein lines of light from the interface are directed at a converging angle substantially equal to a half angle for the Numerical Aperture, and wherein such converging lines of light are directed towards the input window to impact the input window at a location defining a width substantially equal to the window width.

39. A system as claimed in claim 38 wherein the lines of light at the half angle for a Numerical Aperture of the fiber are directed towards the center of the bore.

40. A system as claimed in claim 29 including a fiber optic output for receiving light from the output window.

41. A system as claimed in claim 29 including a fiber optic output for receiving light from the output window, and the fiber optic output having a Numerical Aperture, and wherein the fiber optic output includes a core having an output end face spaced a distance from the output window, the end face having an interface with a cladding and wherein output lines of light from the output window define an angular diverging angle related to the Numerical Aperture, the diverging angle being such that when lines of light from the interface of the output window impact the output fiber, such lines define a width at least substantially no wider than the width of the end face of the fiber optic output.

42. A system as claimed in claim 41 wherein the diverging lines of light emanate from the center of the bore.

43. A system as claimed in claim 29 wherein the capillary tube includes a coating and the windows are formed by selective removal of the coating.

44. A system as claimed in claim 33 wherein the capillary tube includes a coating and the windows are formed by selective removal of the coating.

45. A system as claimed in claim 34 wherein the capillary tube includes a coating and the windows are formed by selective removal of the coating.

46. A system as claimed in claim 37 wherein the capillary tube includes a coating and the windows are formed by selective removal of the coating.

47. A system as claimed in claim 38 wherein the capillary tube includes a coating and the windows are formed by selective removal of the coating.

48. A system as claimed in claim 41 wherein the capillary tube includes a coating and the windows are formed by selective removal of the coating.

49. A system as claimed in claim 29 including multiple input windows spaced from each other and multiple output windows, the windows spaced from each other.

50. A system as claimed in claim 29 wherein the input window is located radially opposite the output window.

51. A system as claimed in claim 49 wherein respective input windows are related to radially opposite output windows.

52. A system as claimed in claim 29 wherein the windows have a rectangular cross-section.

53. A capillary electrophoresis optical system comprising a capillary tube having a bore with a center, an inner surface defining the bore with a selected diameter, an outer surface, a wall thickness of the tube being defined between the surfaces, the bore being for transporting fluid past an optical path, an optical input to the tube and an optical output to the tube, and wherein the bore diameter defines a LaGrange Invariant, and wherein the optical path between the input and output conforms to the LaGrange Invariant.

54. A system as claimed in claim 53 including a fiber optic input for directing input light to the optical input, and wherein the fiber optic input defines a Numerical Aperture and wherein the Numerical Aperture is related to the LaGrange Invariant of the tube.

55. A system as claimed in claim 53 including an fiber optic output for receiving output light from the optical output, and wherein the fiber optic output defines a Numerical Aperture, and wherein the Numerical Aperture is related to the LaGrange Invariant of the tube.

56. A system as claimed in claim 54 including a fiber optic output for receiving output light from the output window, and defines a Numerical Aperture, and wherein the Numerical Aperture is matched in relation to the LaGrange Invariant of the tube.

57. A capillary electrophoresis optical system comprising a capillary tube having a bore with a center, an inner surface defining the bore with a selected diameter, an outer surface, and a wall thickness of the tube defined between the surfaces, the bore being for transporting fluid past an optical path, a fiber optic input for directing input light to the capillary, and wherein the fiber optic input includes a core having an end face spaced a distance from the input window whereby light is transmitted from the fiber optic input end face, the end face having an interface with a cladding and wherein light from the interface is directed at a converging angle related to a Numerical Aperture of the fiber input, a fiber optic output for receiving light from the capillary, and wherein the fiber optic output includes a core having an output end face spaced a distance from the capillary, the fiber optic output including a core having an interface with a cladding and wherein light is directed towards the interface, and wherein the light direction from the interface define a LaGrange Invariant for the optical path.

58. A system as claimed in claim 57 wherein the LaGrange Invariant is defined by a Numerical Aperture of the fiber optic input and fiber optic output.

* * * * *